United States Patent
Nishikaze

(10) Patent No.: US 10,712,338 B2
(45) Date of Patent: Jul. 14, 2020

(54) METHOD OF PREPARING SAMPLE FOR ANALYSIS AND ANALYSIS METHOD

(71) Applicant: SHIMADZU CORPORATION, Kyoto-shi, Kyoto (JP)

(72) Inventor: Takashi Nishikaze, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 142 days.

(21) Appl. No.: 15/562,698

(22) PCT Filed: Mar. 31, 2016

(86) PCT No.: PCT/JP2016/060782
§ 371 (c)(1),
(2) Date: Sep. 28, 2017

(87) PCT Pub. No.: WO2016/159291
PCT Pub. Date: Oct. 6, 2016

(65) Prior Publication Data
US 2018/0059094 A1 Mar. 1, 2018

(30) Foreign Application Priority Data

Mar. 31, 2015 (JP) ................................ 2015-071550
May 25, 2015 (JP) ................................ 2015-105289

(51) Int. Cl.
| | | |
|---|---|---|
| G01N 33/00 | (2006.01) |
| G01N 33/50 | (2006.01) |
| C07H 1/00 | (2006.01) |
| G01N 27/62 | (2006.01) |
| G01N 33/68 | (2006.01) |
| H01J 49/00 | (2006.01) |

(52) U.S. Cl.
CPC ............... *G01N 33/50* (2013.01); *C07H 1/00* (2013.01); *G01N 27/62* (2013.01); *G01N 33/6848* (2013.01); *H01J 49/0031* (2013.01); *G01N 2400/00* (2013.01); *G01N 2440/38* (2013.01); *G01N 2560/00* (2013.01); *H01J 49/00* (2013.01)

(58) Field of Classification Search
CPC ..................................................... G01N 33/50
USPC ........................................................ 436/173
See application file for complete search history.

(56) References Cited

FOREIGN PATENT DOCUMENTS

| | | |
|---|---|---|
| JP | 2013-068594 A | 4/2013 |
| JP | 2013-076629 A | 4/2013 |

(Continued)

OTHER PUBLICATIONS

Translation of JP2015034712, obtained Jul. 8, 2019 (Year: 2019).*

(Continued)

*Primary Examiner* — Christine T Mui
*Assistant Examiner* — Emily R. Berkeley
(74) *Attorney, Agent, or Firm* — Sughrue Mion, PLLC

(57) ABSTRACT

In the method of preparing a sample for analysis, a reaction is performed that produces different modified product depending on the sialic acid linkage type when a sialic acid is bound to a sugar chain of an analyte. In this reaction, an analyte containing a sugar chain, an amine containing two or more carbon atoms, and a dehydration-condensation agent are used. The sialic acid linkage type can be identified by analyzing the resulting sample with mass spectrometry etc. This method is applicable not only to free sugar chains but also to glycopeptides and glycoproteins.

15 Claims, 10 Drawing Sheets

(56) References Cited

FOREIGN PATENT DOCUMENTS

| JP | 2015-034712 A | 2/2015 |
|---|---|---|
| WO | 2015075139 A1 | 5/2015 |

OTHER PUBLICATIONS

Miura et al. "Rapid and Simple Solid-Phase Esterification of Sialic Acid Residues for Quantitative Glycomics by Mass Spectrometry" Chem. Eur. J. 2007, 13, 4797-4804 (Year: 2007).*
Toyoda et al. "Quantitative Derivatization of Sialic Acids for the Detection of Sialoglycans by MALDI MS" Anal. Chem. 2008, 80, 5211-5218 (Year: 2008).*
William R. Alley, Jr. et al., "Glycomic Analysis of Sialic Acid Linkages in Glycans Derived from Blood Serum Glycoproteins," Journal of Proteome Research, 2010, pp. 3062-3072, vol. 9, No. 6.
Karli R. Reiding et al., "High-Throughput Profiling of Protein N-Glycosylation by MALDITOF-MS Employing Linkage-Specific Sialic Acid Esterification," Analytical Chemistry, 2014, 16 pgs, vol. 17, No. 12.
Susan F. Wheeler et al., "Derivatization of sialic acids for stabilization in matrix-assisted laser desorption/ionization mass spectrometry and concomitant differentiation of $\alpha(2\rightarrow3)$- and $\alpha(2\rightarrow6)$-isomers," Rapid Communications in Mass Spectrometry, 2009, pp. 303-312, vol. 23.
International Search Report for PCT/JP2016/060782, dated Jun. 28, 2016 (PCT/ISA/210).
Noortje de Haan, et al., "Linkage-Specific Sialic Acid Derivatization on MALDI-TOF-MS Profiling of IgG Glycopeptides", Analytical Chemistry, Jul. 31, 2015, vol. 87, No. 16, pp. 8284-8291.
Communication dated Oct. 30, 2018, from European Patent Office in counterpart application No. 16773171.0.
Non-Final Office Action dated Jul. 18, 2019 issued by the United States Patent and Trademark Office in U.S. Appl. No. 15/846,458.
Yang et al., "Integrated Glycoprotein Immobilization Method for Glycopeptide and Glycan Analysis of Cardiac Hypertrophy", Anal Chem. Oct. 6, 2015. vol. 87, No. 19, pp. 9671-9678, 17 pages total.
Shah, P., et al., "Mass Spectrometric Analysis of Sialylated Glycans with Use of Solid-Phase Labeling of Sialic Acids", Analytical Chemistry, 2013, vol. 85, pp. 3606-3613 (8 pages).
Communication dated Jan. 25, 2019 from the State Intellectual Property Office of the P.R.C.in application No. 201680020438.3.

* cited by examiner

METHOD OF PREPARING SAMPLE FOR ANALYSIS AND ANALYSIS METHOD

CROSS REFERENCE TO RELATED APPLICATIONS

This application is a National Stage of International Application No. PCT/JP2016/060782 filed Mar. 31, 2016, claiming priority based on Japanese Patent Application No. 2015-071550, filed Mar. 31, 2015 and Japanese Patent Application 2015-105289, filed May 25, 2015, the contents of all of which are incorporated herein by reference in their entirety.

TECHNICAL FIELD

The present invention relates to a method of preparing a sample for analysis and an analysis method using the obtained sample for analysis.

BACKGROUND ART

Glycosylation of peptide chains is one of the most important processes of post-translational modification. Glycoproteins containing sugar chains attached to peptide chains are involved in various life phenomena. It is believed that, in vivo, intercellular signal transduction, molecular recognition, etc. are controlled by precisely recognizing slight structural differences of sugar chains Therefore, structural analysis of glycoproteins or glycopeptides is expected to make a major contribution to elucidation of life phenomena, drug discovery, biomarker development, etc.

An N-linked sugar chain attached to an asparagine residue of a protein has at least one branch, and often has sialic acid at its non-reducing end. Sialic acid at the non-reducing end of a sugar chain is directly involved in molecular recognition, and therefore the analytical determination of the presence or absence of sialic acid (the number of sialic acid residues) and the linkage type of sialic acid is important in structural analysis of glycoproteins or glycopeptides.

Sialic acid has a negative charge, and is unstable and is therefore easily decomposed or detached from sugar chains. For this reason, some analytical methods have been proposed in which sialic acid is stabilized by chemical modification before analysis. For example, Patent Document 1 discloses a method in which the reducing end of a free sugar chain is immobilized on a solid-phase carrier, and the carboxy group of sialic acid at the non-reducing end of the sugar chain is methylamidated using PyAOP as a condensation agent and methylamine hydrochloride as a nucleophile. Further, Patent Document 1 discloses an example in which a sample after modification by methylamidation is subjected to mass spectrometry to perform quantitative determination and structural analysis of the sugar chain.

Patent Document 2 states that the detachment of sialic acid during mass spectrometry (ionization) is prevented by modifying (or removing) all the carboxy groups present in a glycopeptide by reaction in the presence of a dehydration-condensation agent such as a phosphonium salt. Further, Patent Document 2 states that the branching structure of sialic acid-containing sugar chain of a glycopeptide can be analyzed by subjecting a sample after modification to multi-stage mass spectrometry.

Mass spectrometry is an effective analysis method for structural analysis of sugar chains. As described above, the presence or absence of sialic acid and the branching structure of a sugar chain can also be analytically determined by structurally stabilizing sialic acid at the non-reducing end by modification. On the other hand, the methods disclosed in Patent Document 1 and Patent Document 2 cannot identify the linkage type of sialic acid, because methylamidation is performed independently of the linkage type of sialic acid.

As the linkage types of sialic acid to the non-reducing end of a sugar chain, there are mainly $\alpha 2,3$- and $\alpha 2,6$-linked isomers. It is known that in vivo, a difference in the linkage type of sialic acid is involved in various life phenomena. For example, it is known that the linkage type of sialic acid changes with canceration. Therefore, identifying a difference in the linkage type of sialic acid is attracting attention as a biomarker or in quality control of biopharmaceuticals, etc.

In order to identify the linkage type of sialic acid by mass spectrometry, linkage type-specific modification needs to be performed so that sialic acid has a mass different depending on its linkage type. For example, Patent Document 3 proposes a method in which methylesterification of sialic acid is performed using 1-methyl-3-p-tolyltriazene (MTT), and then an acidic condition is created. Patent Document 3 states that this method can discriminate between $\alpha 2,3$-linked sialic acid and $\alpha 2,6$-linked sialic acid, because only $\alpha 2,3$-linked sialic acid is selectively demethylated under an acidic condition.

Further, a method for identifying the linkage type of sialic acid by mass spectrometry has also been proposed which utilizes the fact that $\alpha 2,3$-linked sialic acid easily form a lactone ring by intramolecular dehydration condensation in the presence of a dehydration-condensation agent. For example, Non-Patent Document 1 and Non-Patent Document 2 disclose that when a sugar chain sample and a dehydration-condensation agent are present in methanol or ethanol, $\alpha 2,6$-linked sialic acid is preferentially esterified, and $\alpha 2,3$-linked sialic acid preferentially forms a lactone ring by intramolecular dehydration. Non-Patent Document 3 discloses a method in which a sugar chain sample is reacted with ammonium chloride to lactonize and amidate $\alpha 2,3$-linked sialic acid and $\alpha 2,6$-linked sialic acid, respectively and then they are completely methylated. When these modification methods are used, a modified compound of $\alpha 2,3$-linked sialic acid and a modified compound of $\alpha 2,6$-linked sialic acid have different masses, which makes it possible to identify the linkage type of sialic acid by mass spectrometry.

PRIOR ART DOCUMENTS

Patent Documents

Patent Document 1: JP-A-2013-68594
Patent Document 2: JP-A-2015-34712
Patent Document 3: JP-A-2013-76629

Non-Patent Documents

Non-Patent Document 1: Wheeler, S. et al., *Rapid Commun. Mass Spectrom.*, vol. 23 pp. 303-312 (2009)
Non-Patent Document 2: Reiding, K. et al, *Anal. Chem.*, vol. 86, pp. 5784-5793 (2014)
Non-Patent Document 3: Alley Jr, W. et al, *J. Proteome Res.* vol. 9, pp. 3062-3072 (2010)

SUMMARY OF THE INVENTION

Problems to be Solved by the Invention

The ester of sialic acid disclosed in Non-Patent Document 1 and Non-Patent Document 2 has a problem that its esterified site is easily detached. The amide compound disclosed in Non-Patent Document 3 is more stable than the ester. However, the modification method disclosed in Non-Patent Document 3 needs to perform amidation under moderate conditions, and therefore the reaction takes much time.

Further, it is difficult to say that the modification reaction of α2,3-linked sialic acid and the modification reaction of α2,6-linked sialic acid in the conventional methods are sufficiently specific, and therefore even when a sugar chain sample containing only α2,3-linked sialic acid is reacted, a modified compound, which is the same as that formed when α2,6-linked sialic acid is reacted, is formed at a high rate. For this reason, there is a problem that it is difficult, when a sugar chain sample contains two or more sialic acid residues, to precisely determine the number of α2,3-linked sialic acid residues and the number of α2,6-linked sialic acid residues.

Further, the above-described conventional techniques are developed for discriminating between α2,3-linked sialic acid and α2,6-linked sialic acid of a free sugar chain, and no modification methods have heretofore been reported which are capable of discriminating between α2,3-linked sialic acid and α2,6-linked sialic acid of a glycopeptide. Glycopeptides tend to be more difficult to analyze than free sugar chains because various side reactions are likely to be induced due to the presence of a peptide moiety. The present inventor actually applied the modification method disclosed in Non-Patent Document 2 to a glycopeptide to perform mass spectrometry. As a result, an obtained analytical sample could not withstand analysis because many side reaction signals were observed (see FIG. 9(B)). For this reason, there has been a demand for the development of a method applicable not only to free sugar chains but also to glycopeptides.

Means for Solving the Problems

In light of the above circumstances, the present inventor has investigated, and as a result has found that the presence or absence of sialic acid and the number of sialic acid residues can be determined, the linkage type of sialic acid can be identified, and the ratio between linkage types of sialic acid can be quantitatively determined by performing a specific modification reaction on a sugar chain-containing sample, and this specific modification reaction can be applied also to glycopeptides.

The present invention relates to a method for preparing an analytical sample for analyzing a sugar chain contained in a sample. As the sample, one containing a free sugar chain or a glycopeptide is preferably used. In the method for preparing an analytical sample according to the present invention, when sialic acid is bound to the sugar chain of an analyte, a reaction (first reaction) is performed to form a modified product that is different depending on the linkage type of sialic acid.

In the first reaction, a reaction among an analyte containing a sugar chain (e.g., a sugar chain or a glycopeptide), an amine containing two or more carbon atoms, and a dehydration-condensation agent is performed. The dehydration-condensation agent used in the first reaction is preferably a carbodiimide. The amine is preferably an alkylamine having a branched alkyl group or a salt thereof. More specifically, the amine is preferably a primary alkylamine or a salt thereof. Particularly, isopropylamine or a salt thereof is preferred.

When sialic acid is bound to the sugar chain of an analyte, a modified product is formed by the first reaction which is different depending on the linkage type of sialic acid. For example, when the sugar chain has α2,3-linked sialic acid, a lactone is formed as a modified product, and when the sugar chain has α2,6-linked sialic acid, an amide is formed as a modified product.

The analyte after the first reaction may further be subjected to another reaction. For example, when the sample to be analyzed contains α2,3-linked sialic acid, a second reaction may be performed to form another modified product from the lactone formed by the first reaction.

In this second reaction, for example, a reaction using an amine is performed. When a lactone is formed from α2,3-linked sialic acid by the first reaction, an amidated product is obtained by performing the second reaction. In this case, the amine used in the second reaction is preferably selected such that an amide that can be formed by the first reaction from α2,6-linked sialic acid and an amide that can be formed by the second reaction from a lactone derived from α2,3-linked sialic acid have different masses. In the second reaction, in addition to the amine, a phosphonium-based dehydration-condensation agent or an uronium-based dehydration-condensation agent is preferably used.

The first reaction and the second reaction may be performed in a state where the analyte is immobilized on a solid-phase carrier.

Further, the present invention relates to a method of analyzing a sample prepared by the method described above. As the analysis method, mass spectrometry is useful.

The present invention can be applied also to peptides or proteins. When the first reaction described above is applied to a peptide or protein, its sialic acid site is preferentially modified. That is, one embodiment of the method of preparing a sample for analysis according to the present invention is a method in which, when sialic acid is bound to an analyte, its sialic acid site is preferentially modified. This embodiment can be applied to structural analysis to, for example, determine the presence or absence of sialic acid in a peptide or protein. Since the presence or absence of sialic acid can be determined, the present invention can be used also for analysis of sialic acid-free peptides or proteins. The sample to be analyzed in this embodiment is a peptide or a protein, preferably a glycopeptide or a glycoprotein. In this embodiment, an amine having less than 2 carbon atoms may be used.

Effects of the Invention

By performing the above-described modification reaction on a sugar chain-containing sample and analyzing an obtained sample, the linkage type of sialic acid can be identified, and the ratio between linkage types of sialic acid can be quantitatively determined. Further, the above-described modification reaction can be applied not only to free sugar chains but also to glycopeptides, and can also be applied to the identification of the linkage type of sialic acid of a glycopeptide etc.

BRIEF DESCRIPTION OF THE DRAWINGS

FIG. 2-1 shows graphs illustrating the ratio between modified products formed when sialylactose was reacted with an amine hydrochloride at 37° C., wherein FIG. 2-1(A) is a graph obtained by reaction between 3'-sialyllactose and an amine, and FIG. 2-1(B) is a graph obtained by reaction between 6'-sialyllactose and an amine.

FIG. 2-2 shows graphs illustrating the ratio between modified products formed when sialylactose was reacted with an amine hydrochloride in an ice bath, wherein FIG. 2-2(A) is a graph obtained by reaction between 3'-sialyllactose and an amine, and FIG. 2-2(B) is a graph obtained by reaction between 6'-sialyllactose and an amine.

FIG. 4 shows negative ion mass spectra of reaction products between a sample of free sugar chains released from fetuin and an amine, wherein FIG. 4(A) is a negative ion mass spectrum obtained by performing only reaction with methylamine hydrochloride, FIG. 4(B) is a negative ion mass spectrum obtained by performing reaction with methylamine hydrohloride after reaction with isopropylamine hydrohloride, and FIG. 4(C) is a negative ion mass spectrum obtained by performing hydrolysis-induced lactone ring opening after reaction with isopropylamine hydrochloride and then performing reaction with methylamine hydrochloride.

FIG. 5 shows negative ion mass spectra of reaction products obtained by reacting free sugar chains released from fetuin and immobilized on a carrier with isopropylamine hydrochloride and then with methylamine hydrochloride, wherein FIG. 5(A) is a negative ion mass spectrum obtained by performing reaction with methylamine hydrochloride after reaction with isopropylamine hydrochloride, and FIG. 5(B) is a negative ion mass spectrum obtained by performing hydrolysis-induced lactone ring opening after reaction with isopropylamine hydrochloride and then performing reaction with methylamine hydrochloride.

FIG. 6-1(A) is a negative ion mass spectrum of a reaction product between 2,3-SGP and isopropylamine, and FIG. 6-1(B) is a negative ion mass spectrum of a reaction product between 2,6-SGP and isopropylamine.

FIG. 6-2(A) is a positive ion mass spectrum of a reaction product between 2,3-SGP and isopropylamine, and FIG. 6-2(B) is a positive ion mass spectrum of a reaction product between 2,6-SGP and isopropylamine.

MODE FOR CARRYING OUT THE INVENTION

Figure 1:
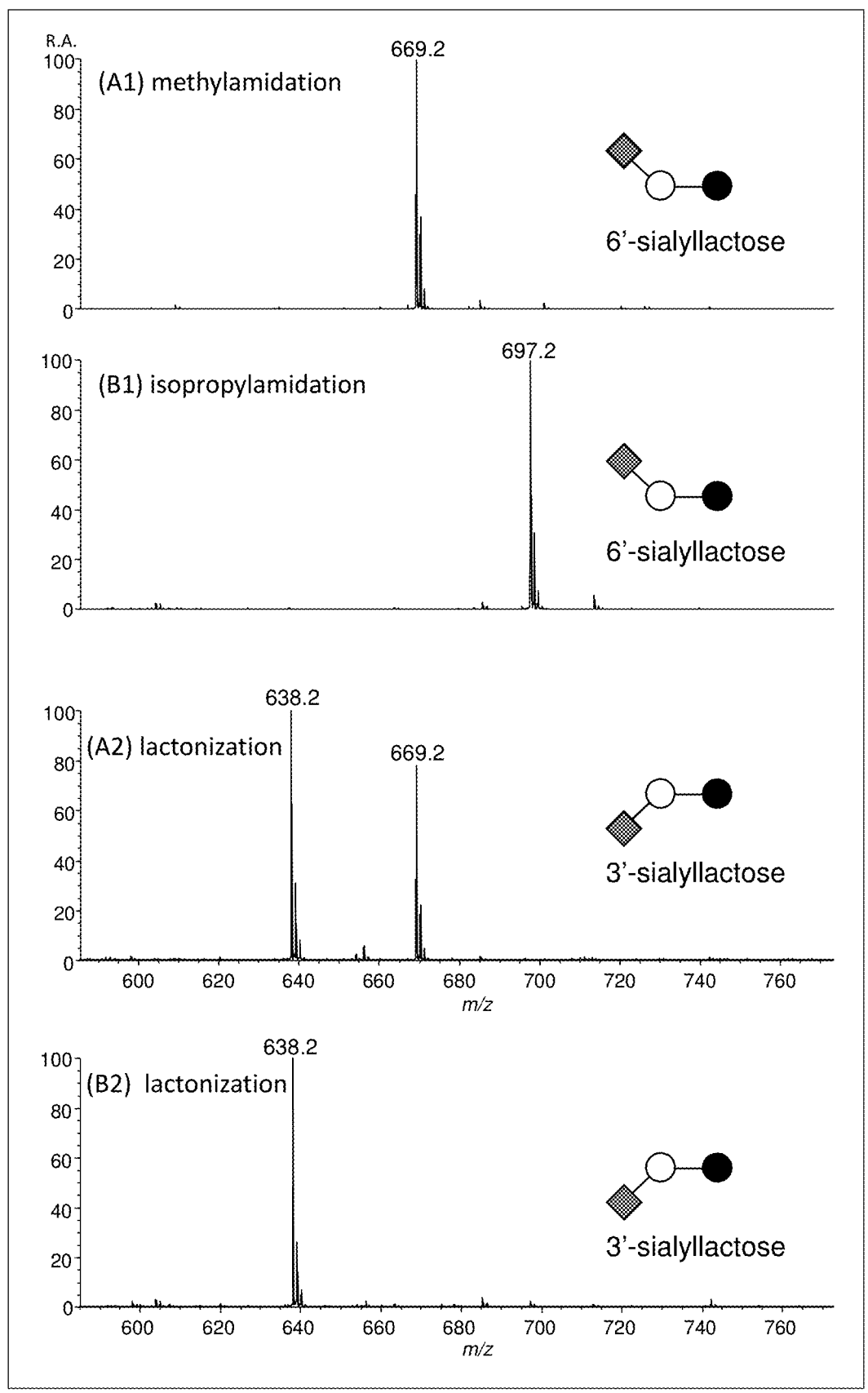
FIG. 1 shows positive ion mass spectra of reaction products between sialyllactose and an amine hydrochloride, wherein FIG. 1(A1) is a positive ion mass spectrum of a reaction product between 6'-sialyllactose and methylamine, FIG. 1(B1) is a positive ion mass spectrum of a reaction product between 6'-sialyllactose and isopropylamine, FIG. 1(A2) is a positive ion mass spectrum of a reaction product between 3'-sialyllactose and methylamine, and FIG. 1(B2) is a positive ion mass spectrum of a reaction product between 3'-sialyllactose and isopropylamine.

The present invention relates to a method of preparing a sample for analysis by modifying a sugar chain, a glycopeptide, or the like for analysis by liquid chromatography, mass spectrometry, or the like.

[Preparation of Sample]

<Sample Containing Sugar Chain>

In the present invention, a sample containing a sugar chain, such as a free sugar chain or a glycopeptide, is used as an analyte. Particularly, a sample for analysis prepared by the method according to the present invention is useful for analytically determining the presence or absence of sialic acid or the linkage type of sialic acid. Therefore, the sample containing a sugar chain is preferably one containing a sugar chain that often has sialic acid at its non-reducing end, such as an N-linked sugar chain or an O-linked sugar chain.

When the analyte is a glycopeptide and the peptide chain of the glycopeptide has a large number of amino acid residues, the peptide chain is preferably cleaved into fragments having a length suitable for analysis by protease digestion or the like. For example, when a sample for mass spectrometry is prepared, the number of amino acid residues of the peptide chain is preferably 30 or less, more preferably 20 or less, even more preferably 15 or less. On the other hand, when it is required to clarify the origin of the peptide to which the sugar chain is bound, the number of amino acid residues of the peptide chain is preferably 2 or more, more preferably 3 or more.

Usually, a protease recognizes an amino acid sequence, and selectively proteolyzes a specific bond of a specific sequence. As such a protease, trypsin, Lys-C, arginine endopeptidase, chymotrypsin, pepsin, or the like is used. It is to be noted that two or more proteases may be used in combination. Alternatively, a protease having low specificity such as thermolysin, proteinase K, or pronase E may be used. Conditions for the protease digestion are not particularly limited, and an appropriate protocol is used depending on the type of protease used. Prior to the protease digestion, denaturation treatment or alkylation treatment of a protein or a peptide in the sample may be performed. Conditions for the denaturation treatment or the alkylation treatment are not particularly limited, and known conditions are appropriately used. It is to be noted that the protease treatment may be performed after modification of the sugar chain.

When the analyte is a free sugar chain, a sugar chain can be released from a glycoprotein or a glycopeptide by a method such as glycosidase treatment using N-glycosidase or O-glycosidase, hydrazinolysis, or β elimination by alkali treatment. When an N-linked sugar chain is released from a peptide chain, N-glycosidase treatment with peptide-N-glycosidase F (PNGase F), peptide-N-glycosidase A (PNGase A), or the like is suitably used. Prior to the glycosidase treatment, the above-described protease digestion may be performed. The reducing end of the sugar chain may be modified by pyridylamination (PA) or the like.

<Modification in the Presence of Dehydration-Condensation Agent and Amine>

The sugar chain-containing sample is chemically modified in the presence of a dehydration-condensation agent and an amine to form a modified product that is different depending on the linkage type of sialic acid at the non-reducing end of a sugar chain. Specifically, a sugar chain having α2,3-linked sialic acid at its non-reducing end is preferentially lactonized by dehydration, and a sugar chain having α2,6-linked sialic acid at its non-reducing end is preferentially amidated.

(Dehydration-Condensation Agent)

As the dehydration-condensation agent, a carbodiimide is preferably used. Examples of the carbodiimide include N,N'-dicyclohexylcarbodiimide (DCC), N-(3-dimethylaminopropyl)-N'-ethylcarbodiimide (EDC), N,N'-diisopropylcarbodiimide (DIC), 1-tert-butyl-3-ethylcarbodiimide (BEC), N,N'-di-tert-butylcarbodiimide, 1,3-di-p-tolylcarbodiimide, bis(2,6-diisopropylphenyl)carbodiimide, bis(trimethylsilyl)carbodiimide, and 1,3-bis(2,2-dimethyl-1,3-dioxolan-4-ylmethyl)carbodiimide (BDDC), and salts thereof.

When an amidation reaction is performed using a carbodiimide as a dehydration-condensation agent and an amine as a nucleophile, a carboxy group present in a site where steric hindrance is large is less likely to be amidated than when a phosphonium-based dehydration-condensation agent (so-called BOP reagent) or an uronium-based dehydration-condensation agent is used as a dehydration-condensation agent. Since the carboxy group of α2,3-linked sialic acid is present at a position where steric hindrance is large, when a carbodiimide is used as a dehydration-condensation agent, amidation is less likely to proceed, and lactonization by intramolecular dehydration is likely to preferentially occur. On the other hand, amidation of the carboxy group of α2,6-linked sialic acid easily proceeds even when a carbodiimide is used as a dehydration-condensation agent. Further, a lactone formed by intramolecular dehydration of the carboxy group of α2,6-linked sialic acid is a 7-membered ring, and has a structure more unstable than that of a lactone formed by intramolecular dehydration of α2,3-linked sialic acid. Therefore, the carboxy group of α2,6-linked sialic acid is preferentially amidated.

In order to promote dehydration condensation and to inhibit a side reaction, a highly nucleophilic additive is preferably used in addition to the carbodiimide. Preferred examples of the highly nucleophilic additive to be used include 1-hydroxybenzotriazole (HOBO, 1-hydroxy-7-azabenzotriazole (HOAt), 4-(dimethylamino)pyridine (DMAP), ethyl 2-cyano-2-(hydroxyimino)acetate (CHA; trade name: OxymaPure), N-hydroxy-succinimide (HOSu), 6-chloro-1-hydroxy-benzotriazole (Cl-HoBt), and N-hydroxy-3,4-dihydro-4-oxo-1,2,3-benzotriazine (HOOBt).

(Amine)

As the amine, a primary or secondary alkylamine containing two or more carbon atoms is used. When an amine having two or more carbon atoms is used, the specificity for lactone formation tends to be higher due to the inhibition of amidation of the carboxy group of α2,3-linked sialic acid as compared to when the number of carbon atoms is 0 (ammonia) or 1 (methylamine). Therefore, the accuracy of identification of the linkage type of sialic acid is enhanced, and the abundance ratio between α2,3-linked sialic acid and α2,6-linked sialic acid etc. is more quantitatively determined. In order to promote lactonization of α2,3-linked sialic acid by dehydration and amidation of α2,6-linked sialic acid and to shorten the reaction time, the number of carbon atoms of the amine is preferably 5 or less, more preferably 4 or less.

Preferred examples of the amine include: primary alkylamines such as ethylamine, propylamine, isopropylamine, butylamine, sec-butylamine, and tert-butylamine; secondary alkylamines such as dimethylamine, ethylmethylamine, diethylamine, propylmethylamine, and isopropylmethylamine; and salts thereof.

Among the above-mentioned amines, when a primary amine is used, the reaction time can be shortened, and the specificity for lactone formation from α2,3-linked sialic acid tends to be high. Further, when an alkylamine having a branched alkyl group, especially isopropylamine is used, the specificity for lactone formation from α2,3-linked sialic acid tends to be high.

Even when an amine having no branched alkyl group is used, the specificity for lactone formation can be enhanced by adjusting the concentration of the dehydration-condensation agent or the reaction temperature. For example, as will be described later in detail with reference to an example, lowering the reaction temperature of the first reaction tends to enhance the specificity for lactone formation from α2,3-linked sialic acid. Further, increasing the concentration of the dehydration-condensation agent also tends to enhance the specificity for lactone formation from α2,3-linked sialic acid.

(Reaction Conditions)

By reacting the sugar chain-containing sample, the dehydration-condensation agent, and the amine, sialic acid of the sugar chain is chemically modified so that a modified product is formed which is different depending on the linkage type of sialic acid. The reaction may be performed in either a liquid phase or a solid phase. When performed in a liquid phase, the reaction in a non-aqueous solvent such as dimethylsulfoxide (DMSO) or dimethylformamide (DMF) is preferred. By performing the reaction in a non-aqueous solvent, a side reaction tends to be inhibited. Therefore, the method according to the present invention can be applied not only to free sugar chains but also to glycopeptides, glycoproteins, or the like.

The concentration of each of the components in the liquid phase reaction is not particularly limited, and can be appropriately determined depending on the type of dehydration-condensation agent or amine used in the reaction. The concentration of the dehydration-condensation agent is, for example, preferably 1 mM to 5 M, more preferably 10 mM to 3 M. When a carbodiimide and a highly nucleophilic additive, such as HOAt or HOBt, are used in combination, their respective concentrations are preferably within the above range. The concentration of the amine is preferably 0.01 M to 20 M, more preferably 0.1 M to 10 M. The reaction temperature is preferably about −20° C. to 100° C., more preferably −10° C. to 50° C. Lowering the reaction temperature tends to enhance the specificity for lactone formation from α2,3-linked sialic acid. On the other hand, excessively lowering the reaction temperature reduces the reaction rate so that unreacted components tend to remain. Therefore, the reaction temperature or time is preferably adjusted depending on the type of amine used etc. so that the specificity for lactone formation is enhanced and the residual amounts of unreacted components are reduced.

The reaction time may be determined depending on the concentrations of the sample and the reagents, the reaction temperature, etc. In the method according to the present invention, modification can be performed in a shorter period of time as compared to a conventionally known method. Therefore, a sample capable of identifying the linkage type of sialic acid can be prepared even when the reaction time is about 1 hour.

When the reaction is performed in a solid phase, any solid-phase carrier can be used without particular limitation as long as an analyte, such as a sugar chain, a glycopeptide, or a glycoprotein, can be immobilized. For example, in order to immobilize a glycopeptide or a glycoprotein, a solid-phase carrier having, as a ligand, an epoxy group, a tosyl group, a carboxy group, an amino group, or the like can be used. Further, in order to immobilize a sugar chain, a solid-phase carrier having, as a ligand, a hydrazide group, an aminooxy group, or the like can be used.

After chemical modification is performed by allowing the dehydration-condensation agent and the amine to act on an analyte immobilized on a solid-phase carrier, a sample may be collected by liberating it from the carrier by a chemical method, an enzymatic reaction, or the like. For example, a glycoprotein or a glycopeptide immobilized on a carrier may be collected by enzymatically cleaving it with PNGase F or trypsin, or a sugar chain immobilized on a solid-phase carrier having a hydrazide group may be collected by liberating it with a weakly acidic solution.

By performing the reaction in a state where an analyte is immobilized on a solid-phase carrier, removal of the reaction reagents or desalting purification is easier, and therefore sample preparation can be simplified. Further, when an analyte is immobilized on a solid-phase carrier in the form of a glycoprotein or a glycopeptide, an enzymatic reaction with PNGase F or the like may be performed after the reaction with the amine and the dehydration-condensation agent to collect a sample after the reaction as a free sugar chain.

If necessary, the sample after the reaction with the dehydration-condensation agent and the amine may be subjected to treatment such as purification, desalting, solubilization, concentration, or drying. These treatments can be performed using known methods.

(Identification of Sialic Acid Linkage Type by Analysis of Modified Product)

As described above, by reacting the sugar chain-containing sample in the presence of the dehydration-condensation agent and the amine having two or more carbon atoms, $\alpha$2,3-linked sialic acid is selectively converted to a lactone by intramolecular dehydration, and $\alpha$2,6-linked sialic acid is selectively amidated. As a result, a sugar chain having $\alpha$2,3-linked sialic acid and a sugar chain having $\alpha$2,6-linked sialic acid are modified with compounds having different functional groups. Therefore, they can be separated from each other by liquid chromatography (LC) or the like, which makes it possible to identify the linkage type of sialic acid.

Further, a lactonized product derived from $\alpha$2,3-linked sialic acid and an amidated product derived from $\alpha$2,6-linked sialic acid have different molecular weights. For example, when ethylamine is used, the amidated product has a molecular weight larger by 45 than that of the lactonized product, and when isopropylamine is used, the amidated product has a molecular weight larger by 59 than that of the lactonized product. By performing the above-described modification reaction on linkage isomers having the same molecular weight, as described above, modified products having different molecular weights can be obtained. Therefore, they can be discriminated by mass spectrometry from each other, which makes it possible to identify the linkage type of sialic acid.

Further, the linkage type of sialic acid can be identified also by analysis using a combination of chromatography and mass spectrometry, such as LC-MS. For example, in the case of LC-MS, the linkage isomers can be discriminated based on mass, and therefore more accurate quantitative determination can be achieved even when the linkage isomers cannot be completely separated from each other by LC.

<Further Modification of Lactonized Product (Second Reaction)>

After the modification by the reaction with the dehydration-condensation agent and the amine, another reaction (second reaction) may further be performed. It is known that the lactonized product formed by intramolecular dehydration of an $\alpha$2,3-sialyl sugar chain is unstable and is decomposed in 50 hours by dissolving it in water (see, for example, Wheeler, S F et al., *Rapid Commun. Mass Spectrometry*, 23 (2009) 303-312). Therefore, when a liquid matrix is used in mass spectrometry, there is a case where some lactone rings open before measurement so that quantitativity is impaired.

By performing the second reaction, another modified product can be formed from the $\alpha$2,3-linked sialic acid-derived lactone to achieve structural stabilization. The another modified product formed from the lactone is not particularly limited as long as it has a different mass from the $\alpha$2,6-linked sialic acid-derived amidated product. Particularly, amidation using an amine is preferred because an amine is highly reactive with the lactonized product, and an almost completely different modified product can be formed.

When an amine having a molecular weight different from that of the amine used in the previous modification (first reaction) is used in the second reaction, an amidated product is obtained which is different in mass from the $\alpha$2,6-linked sialic acid-derived amidated product formed by the first reaction. Further, the use of an isotope-labeled amine in either the first reaction or the second reaction makes it possible to obtain amidated products different in mass even when amines having the same structure or structural isomers of an amine are used in the first reaction and the second reaction.

The amine used in the second reaction is not particularly limited as long as it is different in mass from the amine used in the first reaction. From the viewpoint of facilitating the reaction and enhancing quantitativity, an amine having high reactivity with the $\alpha$2,3-linked sialic acid-derived lactone is preferably used. Ring-opening amidation is caused by the nucleophilic reaction of an amine with the carbonyl of a lactone. The carbonyl of an $\alpha$2,3-linked sialic acid-derived lactone is present in a site where steric hindrance is large, and therefore an amine having a small molecular volume is preferably used to increase the efficiency of nucleophilic reaction of the amine with the carbonyl. Therefore, the amine used for ring-opening amidation of the lactone is preferably ammonia, an alkylamine having 5 or less carbon atoms, or a salt thereof.

Preferred examples of the amine used in the second reaction include: primary alkylamines such as ammonium salts, methylamine, ethylamine, propylamine, isopropylamine, butylamine, sec-butylamine, and tert-butylamine; secondary alkylamines such as dimethylamine, ethylmethylamine, diethylamine, propylmethylamine, and isopropylmethylamine; and salts thereof. The number of carbon atoms of the alkylamine is preferably 4 or less, more preferably 3 or less. Among the above-mentioned amines, primary alkylamines or salts thereof are preferred, linear primary alkylamines or salts thereof are more preferred, and methyl amine and ethyl amine or salts thereof are particularly preferred.

The amidation of the lactone is preferably performed in the presence of a dehydration-condensation agent. The dehydration-condensation agent is preferably one that highly efficiently reacts even with a carbonyl present in a site where steric hindrance is large. For example, the dehydration-condensation agent is preferably a phosphonium-based dehydration-condensation agent or an uronium-based dehydration-condensation agent.

Examples of the phosphonium-based dehydration-condensation agent include (benzotriazol-1-yloxy)tris(dimethylamino)phosphonium (BOP), benzotriazol-1-yl-oxy-tris(pyrrolidino)phosphonium hexafluorophosphate (PyBOP), bromo-tris(dimethylamino)phosphonium hexafluorophosphate (BroP), bromo-tris(pyrrolidino)phosphonium hexafluorophosphate (PyBroP), (7-azabenzotriazol-1-yl-oxy)tris(pyrrolidino)phosphonium hexafluorophosphate (PyAOP), and chloro-tris-pyrrolidinophosphonium hexafluorophosphate (PyCloP). They are collectively called "BOP reagents", and highly efficiently react even with a carboxy group present in a site where steric hindrance is large. Therefore, amidation can be performed with high reaction efficiency even on a site where steric hindrance is large, such as the carboxy group of α2,3-linked sialic acid or the carbonyl of the α2,3-linked sialic acid-derived lactone.

Examples of the uronium-based dehydration-condensation agent include (1-cyano-2-ethoxy-2-oxoethylideneaminooxy)dimethylamino-morpholino-carbenium hexafluorophosphate (COMU), 2-(1H-benzotriazole-1-yl)-1,1,3,3-hexafluorophosphate (HBTU), 2-(7-azabenzotriazol-1-yl)-1,1,3,3-hexafluorophosphate (HATU), 2-(1H-benzotriazole-1-yl)-1,1,3,3-tetramethyluronium tetrafluoroborate (TBTU), 2-(5-norbornene-2,3-dicarboximido)-1,1,3,3-tetramethyluronium tetrafluoroborate (TNTU), and O—(N-succinimidyl)-1,1,3,3-tetramethyluronium tetrafluoroborate (TSTU). Among these uronium salts, COMU is particularly preferred.

Among the above-mentioned dehydration-condensation agents, phosphonium-based dehydration-condensation agents are preferably used from the viewpoint of enhancing the amidation efficiency of the lactone. Further, in order to accelerate the reaction, a base such as N-methylmorpholine is preferably added so that its concentration is about 0.01 to 80% by weight of the total weight of a reaction system. By adding such a base to a reaction system at a concentration within the above range, reaction efficiency can be increased, and the occurrence of a side reaction, the precipitation of other reagents, etc. can be prevented. When N-methylmorpholine is contained as a base in a reaction system, its concentration is preferably 1 to 50% by weight, more preferably 10 to 40% by weight, even more preferably 15 to 30% by weight. Conditions for the amidation (reaction temperature, reaction time, etc.) are not particularly limited, and conventionally known conditions for amidation of sialic acid can be used without change.

The amine used in the second reaction is particularly preferably methylamine hydrochloride because its reactivity is high and a side reaction is less likely to occur. Particularly, when methylamine hydrochloride, PyAOP, and N-methylmorpholine are used, the lactone can be almost completely converted to a methylamide, which makes it possible to achieve high-accuracy quantitative analysis.

After the first reaction and before the amidation by the second reaction, a ring-opening reaction of the α 2,3-linked sialic acid-derived lactone may be performed. As described above, it is known that the lactonized product formed by intramolecular dehydration of α 2,3-sialyl sugar chain is hydrolyzed even in water. Therefore, the lactone is subjected to hydrolysis with time to cause ring-open by simply dissolving, in water (or eluting with water), a sample obtained after the first reaction using a dehydration-condensation agent and an amine.

In order to promote the ring opening of the lactone, an acid or a base is preferably used. Particularly, a base is preferably used because the lactone is easily hydrolyzed by a base. It is to be noted that when the amidation is performed after the ring opening of the lactone, it is preferred that the residual base does not inhibit the amidation or cause a side reaction. When the same amine as the amine used for the amidation after ring opening is used as the base, the above-described problem caused by the remaining base after the ring-opening reaction can be eliminated. It is to be noted that a hydrochloride is preferably used for the amidation, whereas an amine that is not in the form of a salt is preferably used as the base for promoting the ring opening of the lactone.

The ring opening of the lactone performed before the amidation by the second reaction reduces steric hindrance and facilitates the access of the amine to the carbonyl of sialic acid. Therefore, the ring opening performed before the amidation enhances the reaction efficiency of the amidation and reduces the amount of the residual lactone, which further enhances the accuracy of quantitative analysis.

The above-described amidation and ring-opening reaction of the lactone by hydrolysis before the amidation can also be performed in a solid phase. When the first reaction is performed in a state where an analyte is immobilized on a solid phase, the second reaction may be performed while the analyte after the first reaction remains immobilized on the solid phase. Alternatively, the second reaction may be performed by immobilizing an analyte after the first reaction on a solid phase. As a solid-phase carrier, the same one as described above with reference to the first reaction can be used. Conditions for immobilization or liberation of a sample on or from the solid-phase carrier may also be the same as those described above with reference to the first reaction.

[Analysis of Sample]

By subjecting the sample for analysis prepared by the above-described method to liquid chromatography (LC) or mass spectrometry, the linkage type of sialic acid can be identified, or information such as the ratio between linkage types or the presence or absence of sialic acid can be obtained.

For example, in LC analysis, a lactone derived from α2,3-linked sialic acid and an amide derived from α2,6-linked sialic acid are detected as different peaks, which makes it possible to discriminate between an α2,3-sialyl sugar chain and an α2,6-sialyl sugar chain. Further, the ratio between them can also be quantitatively determined based on peak area.

Further, since the lactone derived from α2,3-linked sialic acid and the amide derived from α2,6-linked sialic acid have different masses, signals are detected at different m/z in mass spectrometry. Further, even when the lactone is amidated by the second reaction, since an amine used in the second reaction for amidation to obtain an α2,3-linked sialic acid-derived amide and an amine used in the first reaction for amidation to obtain the α2,6-linked sialic acid-derived amide have different molecular weights, signals corresponding to these amides are detected at different m/z in mass spectrometry.

In mass spectrometry, the quantitative determination of a sugar chain or the structural analysis of a sugar chain can also be performed based on m/z value or peak intensity (peak height, peak area, etc.). Examples of an ionization method for mass spectrometry include matrix-assisted laser desorption ionization (MALDI), electrospray ionization (ESI), and nano-electrospray ionization (nano-ESI). Particularly, MALDI is suitable. The analytical sample obtained by the method according to the present invention can identify the linkage type of sialic acid in either positive ion mode or negative ion mode.

Further, a sample separated by LC and detected as a peak may be subjected to mass spectrometry. When sample separation is performed by LC, LC-MS equipped with LC as a preliminary stage of mass spectrometry may be used, in which case an eluate from LC may be directly ionized and subjected to analysis. Alternatively, the eluate from the LC may be fractionated once and then subjected to mass spectrometry. An LC column is not particularly limited, and may be appropriately selected from, for example, hydrophobic columns such as C30, C18, C8, and C4 generally used for peptide analysis and carriers for hydrophilic affinity chromatography.

Mass spectrometry may be performed in multiple stages of $MS^2$ or more. By performing multi-stage mass spectrometry such as $MS^2$ or more, the structure of a sugar chain or the structure of a peptide moiety to which a sugar chain is bound can also be analyzed in addition to the linkage type of sialic acid. The structural analysis of a sugar chain or a glycopeptide can be performed also by database search using spectral data.

[Application to Peptides and Proteins]

As described above, the method according to the present invention is applicable not only to free sugar chains but also to peptides or proteins. When the preparation method according to the present invention is applied to a glycopeptide or a glycoprotein, it is possible not only to identify the linkage type of sialic acid but also to determine the presence or absence of sialic acid.

As described also in Patent Document 2 (JP-A-2015-34712), when the conventional sialic acid modification method is used, not only the carboxy group of sialic acid but also the carboxy group at the C-terminus of a peptide or the carboxy group of an acidic amino acid residue (glutamic acid and aspartic acid) is amidated. Therefore, it is difficult to know which of the carboxy group of a sugar chain and the carboxy group of sialic acid has been amidated without structural analysis. Further, when the conventional modification method is used, there is a case where dehydrating amidation between the amino group at the N-terminus of a peptide moiety and the side chain of a glutamic acid residue (pyroglutamylation) causes a change in the mass of the peptide moiety.

On the other hand, the above-described first reaction using an amine and a dehydration-condensation agent can be applied to glycopeptides because a side reaction is less likely to occur, and in addition, the carboxy group of a peptide is less likely to be amidated, and the carboxy group of sialic acid tends to be selectively modified (amidated or lactonized). Therefore, when a sample does not have sialic acid (including a case where a sample does not have a sugar chain), a modification reaction hardly occurs, and therefore a peak having the same m/z as a peak before the modification reaction is observed in mass spectrometry. When a sample has α2,6-linked sialic acid, an increase in molecular weight due to amidation is observed. Further, when a sample has α2,3-linked sialic acid, a decrease in molecular weight due to dehydration is observed. Therefore, the method of preparing a sample according to the present invention is useful also for determining the presence or absence of sialic acid in addition to identifying the linkage type of sialic acid. In other words, the method of preparing a sample according to the present invention is useful also for the analysis of a sample having a sugar chain to which sialic acid is not bound (a sample in which the presence or absence of sialic acid is unknown).

Further, the mass of a peptide moiety does not change before and after the reaction, which makes it easy to analyze the results of analysis or to compare the results of analysis with database. In addition, the peptide moiety hardly reacts, and thus the carboxy group at the C-terminus of the peptide or the carboxy group of an acidic amino acid residue remains unmodified, which makes it possible to properly perform an enzymatic reaction on a peptide or protein after the first reaction. For example, even when a protease involving an acidic amino acid residue such as Glu-C or Asp-N is used, protease digestion can be properly performed. Therefore, after the first reaction is performed on a glycoprotein, an enzymatic reaction can also be performed to analyze an obtained sugar chain or glycopeptide.

When the conventional modification method is used, since not only the carboxy group of sialic acid but also the carboxy group at the C-terminus of a peptide or the carboxy group of an acidic amino acid residue is modified, ionization efficiency in negative ion mode mass spectrometry is low, which often makes it difficult or impossible to perform analysis. On the other hand, in the first reaction, since a peptide moiety is hardly modified and the carboxy group at the C-terminus of a peptide or the carboxy group of an acidic amino acid residue remains, an obtained sample is easily negatively ionized. Therefore, even in negative ion mode mass spectrometry, highly-sensitive analysis can be performed, and a peptide that is hard to be positively ionized can be analyzed by negative ion mode mass spectrometry. As shown in an example that will be described later, the linkage type of sialic acid of a glycopeptide modified by the method according to the present invention can be identified by either positive ion mode or negative ion mode mass spectrometry.

It is to be noted that depending on the reaction conditions between a glycopeptide and an amine in the presence of a dehydration-condensation agent, there is a case where some or all of the carboxy groups of the peptide are amidated. Even in this case, when an amine containing two or more carbon atoms is used, α2,3-linked sialic acid in the sugar chain moiety is selectively lactonized, and α2,6-linked sialic acid in the sugar chain moiety is selectively amidated, and therefore the linkage type of sialic acid can be identified by a difference in mass caused by a difference in linkage type between them.

When the first reaction is applied to a peptide or a protein, as described above, its sialic acid site is preferentially modified. Therefore, the first reaction can be applied to structural analysis such as the determination of the presence or absence of sialic acid in a peptide or protein. In other words, one embodiment of the method of preparing a sample for analysis according to the present invention is a method in which, when sialic acid is bound to an analyte, its sialic acid site is preferentially modified. The sample to be analyzed used in this embodiment is a peptide or a protein, preferably a glycopeptide or a glycoprotein.

The first reaction of a peptide or protein sample can be performed under the same conditions as that of a sugar chain sample. In more specific, when the reaction is performed in a liquid phase, a peptide or protein sample may be reacted with a dehydration-condensation agent and an amine in a nonaqueous solvent such as DMSO or DMF. This reaction preferentially chemically modifies sialic acid in a sugar chain. As described above, a dehydration-condensation agent and an amine may be allowed to act on a peptide or protein immobilized on a solid-phase carrier. The peptide or protein can be immobilized on the solid-phase carrier via, for example, its N-terminus, C-terminus, or SH group.

When a peptide or protein is subjected to the first reaction, the above-described dehydration-condensation agent and amine are preferably used. For the purpose of identifying the linkage type of sialic acid, as described above, an amine containing two or more carbon atoms is used. In contrast, an amine having less than two carbon atoms, such as an ammonium salt or methylamine or a salt thereof, may be used when it is not necessary to identify the linkage type of sialic acid. When only the presence or absence of sialic acid is analytically determined, it is not necessary to form a modified product different depending on the linkage type of sialic acid. Therefore, even when an amine having less than two carbon atoms is used, such a purpose can be achieved. On the other hand, when an amine having two or more carbon atoms is used and a sample is a gycoprotein or glycopeptide containing sialic acid, in addition to the analytical determination of the presence or absence of sialic acid, identification of the linkage type of sialic acid, analytical determination of the abundance ratio between linkage types of sialic acid, etc. can be performed at the same time.

EXAMPLES

Hereinafter, the present invention will be specifically described with reference to examples, but the present invention is not limited to the following examples. It is to be noted that in the following description, "%" represents % by weight unless otherwise specified.

[Example 1] Modification of Sialyllactose

In Example 1, 3'-sialyllactose was used as a free sugar chain sample having α2,3-linked sialic acid, and 6'-sialyllactose was used as a free sugar chain sample having α2,6-linked sialic acid to examine the effects of the type of amine used and reaction conditions on modification.
(Preparation of Sugar Chain Sample)
3'-sialyllactose and 6'-sialyllactose (both of which were purchased from Tokyo Chemical Industry Co., Ltd.) were each dissolved in water, dispensed, centrifugally concentrated (SpeedVac) to remove the solvent, and dried.
(Reaction with Amine)
Solutions were prepared by dissolving various amine hydrochlorides (ammonium hydrochloride, methylamine hydrochloride, ethylamine hydrochloride, dimethylamine hydrochloride, propylamine hydrochloride, isopropylamine hydrochloride, and butylamine hydrochloride) in DMSO (amine hydrochloride concentration: 1 M to 4 M), and 10 µL of each of the solutions was added to a sugar chain sample. Then, 10 µL of a solution obtained by dissolving diisopropylcarbodiimide (DIC) and 1-hydroxybenzotriazole (HOBt) in DMSO so that their respective concentrations were 500 mM was added as a dehydration-condensation agent. The mixture was stirred at room temperature for 2 minutes and then reacted at 37° C. for 1 hour. Then, the solution after the reaction was diluted by adding 120 µL of a 93.3% acetonitrile (ACN), 0.13% trifluoroacetic acid (TFA) solution.
(Purification of Reaction Product)
As a carrier for purification, cotton HILIC microtip was used. First, the tip end of a 200-µL pipette tip was filled with cotton. Suction and discharge of 200 µL of water were repeated three times by pipetting to perform washing. Then, suction and discharge of 60 µL of a 99% ACN, 0.1% TFA solution were repeated three times to perform equilibration. Pipetting was performed 10 times in the diluted reaction solution to adsorb a sugar chain contained in the reaction solution to the cotton. Then, suction and discharge of 150 µL of a 99% ACN, 0.1% TFA solution were repeated three times to perform washing. Finally, pipetting was performed five times in 20 µL of water to elute the sugar chain into the water.
(Mass Spectrometry)
First, 1 µL of the eluted sample in water was dropped onto a focus plate, and 0.5 µL of a solution obtained by dissolving 10 mg/mL 2,5-dihydroxybenzoic acid (DHB) and 1 mM NaCl in 50% ACN was added as a matrix. After drying, 0.2 µL of ethanol was dropped for recrystallization. This sample was subjected to mass spectrometry in positive ion mode by MALDI-QIT-TOF-MS (AXIMA-Resonance, Shimadzu/Kratos).

The mass spectrum of a sample obtained by reacting 6'-sialyllactose with methylamine is shown in FIG. 1(A1), and the mass spectrum of a sample obtained by reacting 6'-sialyllactose with isopropylamine is shown in FIG. 1(B1). The mass spectrum of a sample obtained by reacting 3'-sialyllactose with methylamine is shown in FIG. 1(A2), and the mass spectrum of a sample obtained by reacting 3'-sialyllactose with isopropylamine is shown in FIG. 1(B2).
(Results of Analysis)
The sample obtained by reacting 6'-sialyllactose having α2,6-linked sialic acid with methylamine in the presence of a dehydration-condensation agent had a peak in the positive ion mass spectrum at m/z 669 (FIG. 1(A1)), and was almost 100% methylamidated. The sample obtained by reacting 6'-sialyllactose with isopropylamine in the presence of a dehydration-condensation agent had a peak in the positive ion mass spectrum at m/z 697 (FIG. 1 (B1)), and was almost 100% isopropylamidated.

The sample obtained by reacting 3'-sialyllactose having a 2,3-linked sialic acid with isopropylamine in the presence of a dehydration-condensation agent had a peak in the positive ion mass spectrum at m/z 638 (FIG. 1 (B2)), and was almost 100% lactonized by dehydration. On the other hand, when 3'-sialyllactose was reacted with methylamine, in addition to the peak of a lactonized product at m/z 638, the peak of a methylamidated product was observed at m/z 669 (FIG. 1(A2)). These results reveal that when a sugar chain having α2,3-linked sialic acid at its non-reducing end is reacted with an amine in the presence of a dehydration-condensation agent, lactonization by dehydration and amidation by nucleophilic reaction of the amine competitively occur, and the ratio between modified products formed varies depending on the type of amine used.

Figures 1, 2:
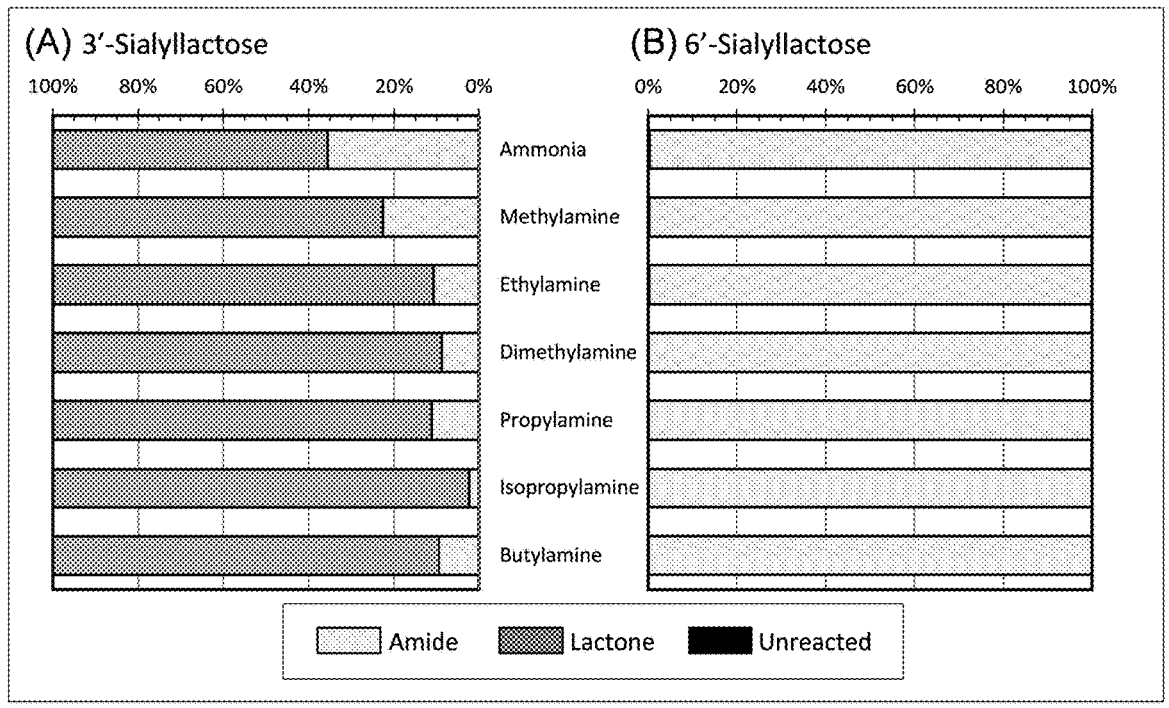
Figure 2:
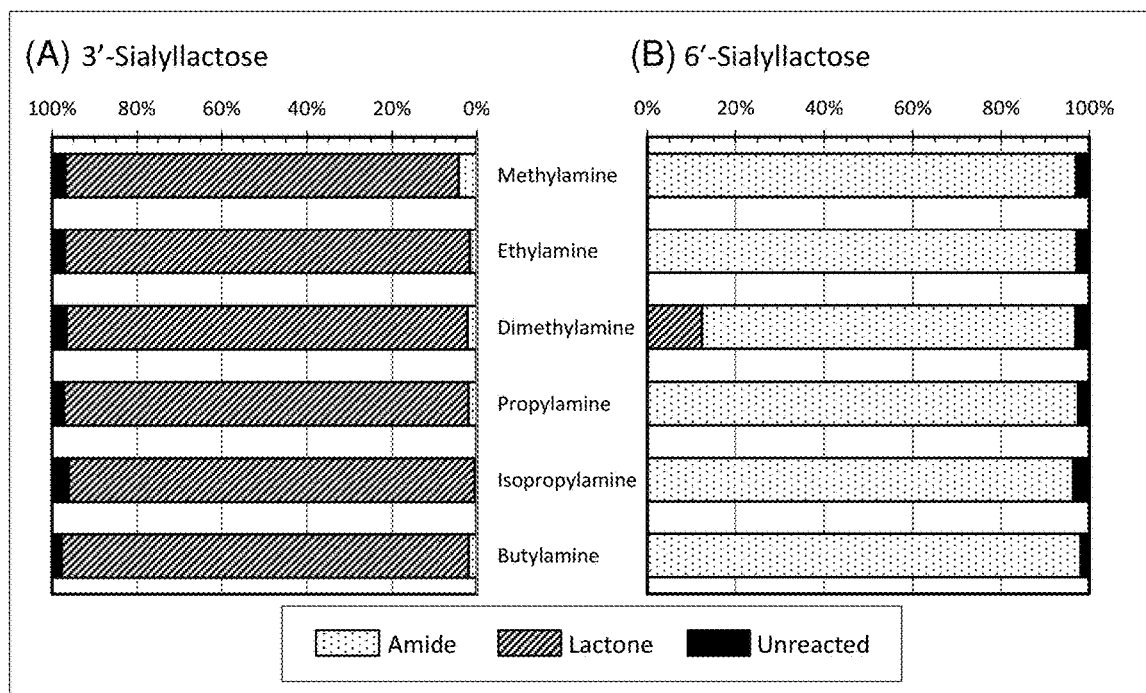
Figures 1, 6:
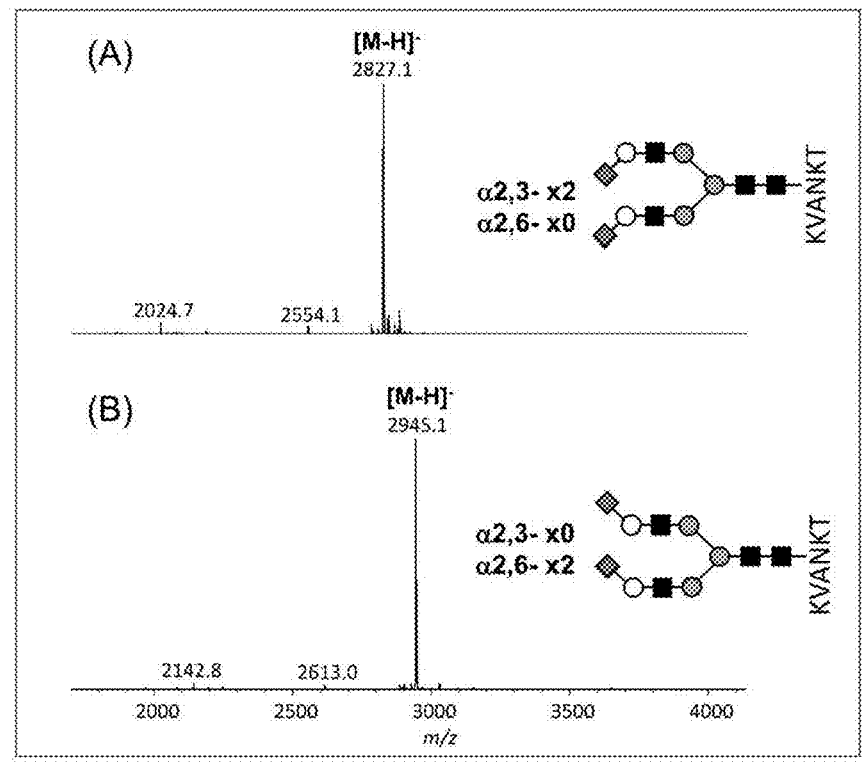
Figures 2, 6:
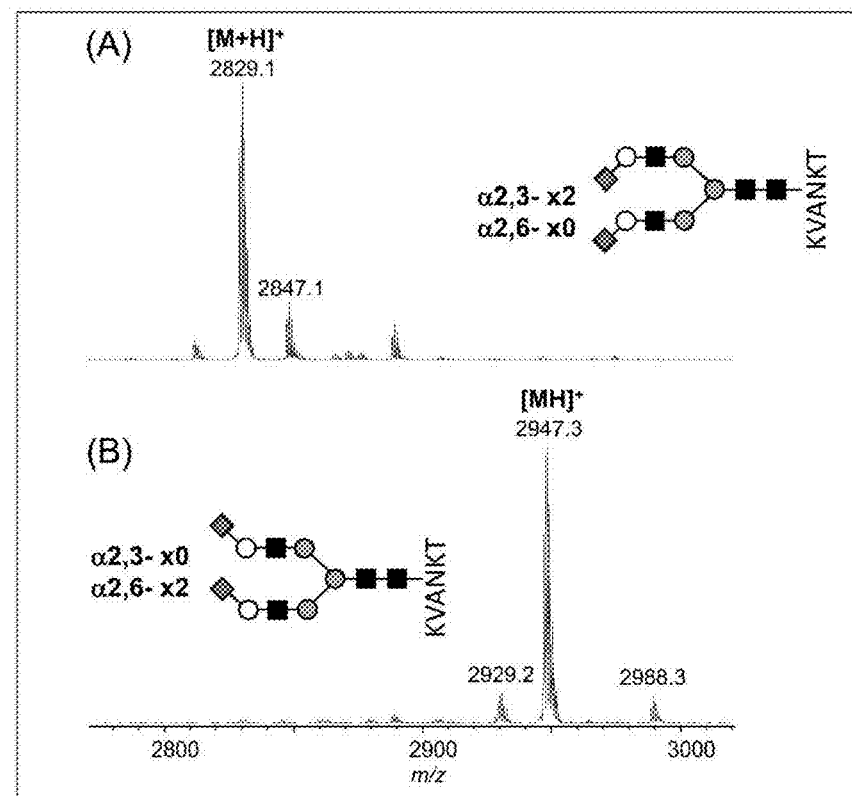

The ratio between modified products formed by the reaction of 3'-sialyllactose and an amine is shown in FIG. 2-1(A). The ratio between modified products formed by the reaction of 6'-sialyllactose and an amine is shown in FIG. 2-1(B). As shown in FIG. 2-1(B), 6'-sialyllactose was almost 100% amidated regardless of the type of amine used, whereas in the case of 3'-sialyllactose, the ratio between lactonization and amidation varied depending on the type of amine used. When ammonia or methylamine was used, the ratio of lactonization was less than 80%, whereas when an amine (ethylamine, dimethylamine, propylamine, isopropylamine, or butylamine) having two or more carbon atoms was used, the ratio of lactonization was high, which indicates that selectivity is excellent. Particularly, when isopropylamine having a branched alkyl group was used, the ratio of lactonization was 95% or more, which indicates that reaction specificity is high.

[Example 2] Examination of Reaction Conditions

In Example 2, sialyllactose was used as a sample, and reacted with an amine in the presence of a dehydration-condensation agent in the same manner as in Example 1. The effects of reaction conditions on modification were examined by changing the concentration of an amine hydrochloride, the concentration of a dehydration-condensation agent, and the temperature during reaction.

(Examination of Amine Concentration)

A reaction between sialyllactose and an amine was performed in the presence of a dehydration-condensation agent (DIC and HOBO in the same manner as in Example 1 except that isopropylamine hydrochloride was used as the amine hydrochloride, and the concentration of isopropylamine hydrochloride during the reaction was varied within the range of 0.5 M to 4.5 M (concentration at the time of preparation of DMSO solution: 1 M to 9 M). Each reaction solution was purified and subjected to mass spectrometry in positive ion mode in the same manner as in Example 1. The reaction specificity of each of the samples was the same as that in Example 1. To be more specific, irrespective of the amine concentration, 3'-sialyllactose formed a lactone with an efficiency of 95% or more, and 6'-sialyllactose was almost 100% isopropylamidated.

(Examination of Concentration of Dehydration-Condensation Agent)

A reaction between sialyllactose and an amine was performed in the presence of a dehydration-condensation agent in the same manner as in Example 1 except that isopropylamine hydrochloride was used as the amine hydrochloride, and the concentrations of dehydration-condensation agent (DIC and HOBt) during the reaction were both varied in the range of 50 mM to 250 mM (concentrations at the time of preparation of DMSO solution: 100 mM to 500 mM). Each reaction solution was purified and subjected to mass spectrometry in positive ion mode in the same manner as in Example 1. The reaction specificity of each of the samples was the same as that in Example 1. To be more specific, irrespective of the amine concentration, 3'-sialyllactose formed a lactone with an efficiency of 95% or more, and 6'-sialyllactose was almost 100% isopropylamidated.

(Examination of Type of Dehydration-Condensation Agent)

A reaction was performed using isopropylamine hydrochloride as an amine hydrochloride and a combination of dicyclohexylacrbodiimide (DCC) instead of DIC and HOBt as a dehydration-condensation agent. Reaction specificity was not changed, and 3'-sialyllactose formed a lactone with an efficiency of 95% or more, and 6'-sialyllactose was almost 100% isopropylamidated. Further, reaction specificities were not changed even when the reaction was performed using a combination of DIC or DCC and 1-hydroxy-7-azabenzotriazole (HOAt), ethyl 2-cyano-2-(hydroxyimino) acetate (OxymaPure), or 4-(dimethylamino)pyridine (DMAP) instead of HOBt.

(Examination of Reaction Temperature)

Isopropylamine hydrochloride as an amine hydrochloride and a dehydration-condensation agent (DIC and HOBt) were added to a sugar chain sample so that the concentration of the amine hydrochloride during reaction was 2 M (concentration at the time of preparation of DMSO solution: 4 M) and the concentrations of dehydration-condensation agent (DIC and HOBO during reaction were both 500 mM (concentrations at the time of preparation of DMSO solution: 1 M), and then the mixture was reacted in an ice bath (at about 0° C.) for 2 hours. Then, the obtained reaction solution was purified and subjected to mass spectrometry in positive ion mode in the same manner as in Example 1. 6'-sialyllactose was almost 100% isopropylamidated as in the case of Example 1. 3'-sialyllactose exhibited a specificity for lactone formation (ratio of a lactone to the total of an amidated product and a lactone) of about 99% that was higher than that in Example 1.

A reaction was performed in an ice bath for 2 hours in the same manner as described above except that methylamine hydrochloride, ethylamine hydrochloride, dimethylamine hydrochloride, propylamine hydrochloride, or butylamine hydrochloride was used as the amine hydrochloride instead of isopropylamine hydrochloride. Then, the obtained reaction solution was purified and subjected to mass spectrometry in positive ion mode.

The ratio between modified products formed by the reaction between 3'-sialyllactose and an amine in an ice bath is shown in FIG. 2-2(A). The ratio between modified products formed by the reaction between 6'-sialyllactose and an amine in an ice bath is shown in FIG. 2-2(B).

The comparison between FIG. 2-1(A) and FIG. 2-2(A) reveals that the specificity for lactone formation was improved by reacting 3'-sialyllactose and an amine at low temperature in the presence of a dehydration-condensation agent, and particularly, when an amine having 2 or more carbon atoms was used, a high specificity of about 98% or more was achieved. It is to be noted that the reaction rate in an ice bath was low, and therefore, as shown in FIG. 2-2, about 2 to 9% of unreacted components were detected after 2 hours from the start of the reaction. It is considered that the unreacted components can be reduced by increasing the reaction time or by increasing the reaction rate by increasing the concentration of the amine or the dehydration-condensation agent.

[Example 3] Modification of Branched Sugar Chains Having Two or More Sialic Acid Residues In Example 3, four biantennary pyridylaminated (PA) sugar chains having two sialic acid residues whose linkage types were known were used as samples. Each of the samples was modified by reaction with an amino hydrochloride in the presence of a dehydration-condensation agent (DIC and HOBt), and the obtained reaction solution was purified and subjected to mass spectrometry in positive ion mode in the same manner as in Example 1.

Figure 3:
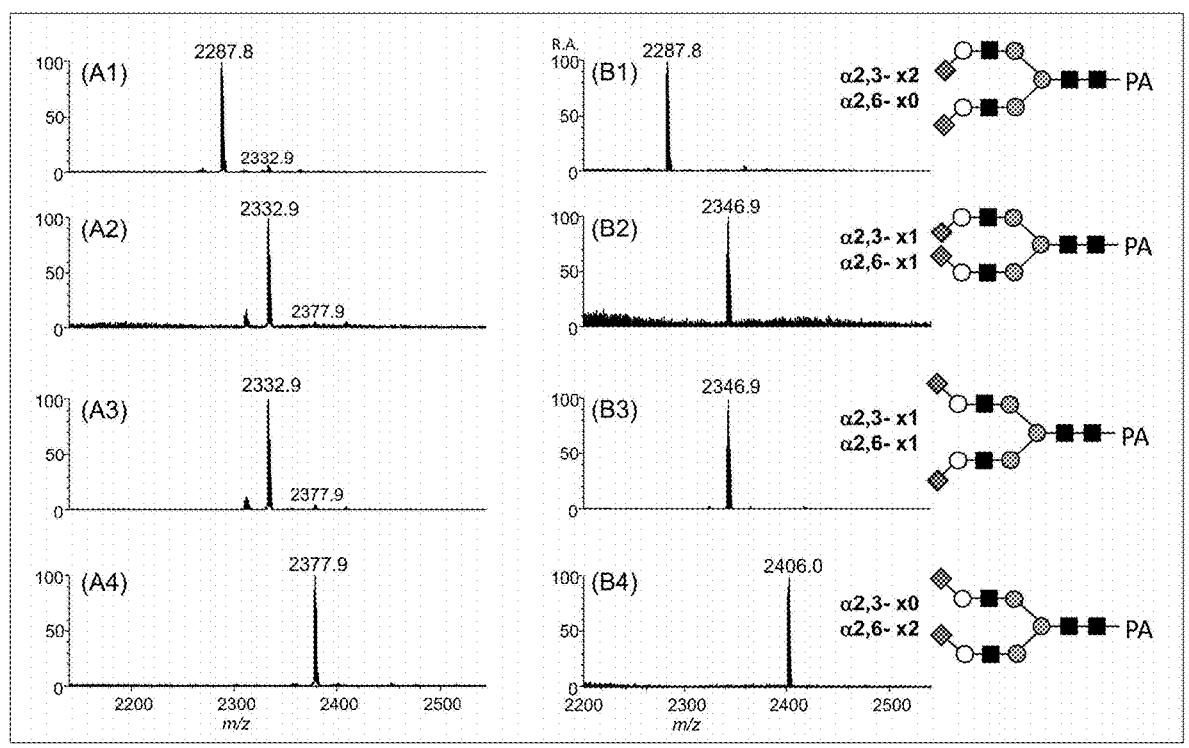
FIG. 3 shows positive ion mass spectra of reaction products between a biantennary pyridylaminated (PA) sugar chain having two sialic acid residues and an amine hydrochloride, wherein FIGS. 3(A1) to 3(A4) are positive ion mass spectra obtained by using ethylamine hydrochloride, and FIGS. 3(B1) to 3(B4) are positive ion mass spectra obtained by using isopropylamine hydrochloride.

Positive ion mass spectra of the samples modified with ethylamine hydrochloride as the amine hydrochloride are shown in FIGS. 3(A1) to 3(A4). Positive ion mass spectra of the samples modified with isopropylamine hydrochloride as the amine hydrochloride are shown in FIGS. 3(B1) to 3(B4).

In the mass spectra of all the four sugar chains before modification, peaks were observed at the same m/z. In contrast, when the sugar chains were reacted with an amine hydrochloride, peaks were observed which had different m/z depending on the linkage type of sialic acid present in the molecule and the number of sialic acid residues. Specifically, in the case of using ethylamine hydrochloride, when the two sialic acid residues were both α2,3-linked sialic acid residues, both of them were lactonized so that a peak was observed at m/z 2288 (FIG. 3(A1)); when one of the two sialic acid residues was an α2,3-linked sialic acid residue and the other was an α2,6-linked sialic acid residue, one sialic acid residue was lactonized and the other sialic acid residue was ethylamidated, so that a peak was observed at m/z 2333 (FIGS. 3(A2) and 3(A3)); and when the two sialic acid residues were both α2,6-linked sialic acid residues, both of them were ethylamidated so that a peak was observed at m/z 2378 (FIG. 3(A4)). In the case of using isopropylamine hydrochloride, when the two sialic acid residues were both lactonized, a peak was observed at m/z 2288 as in the case of using ethylamine hydrochloride (FIG. 3(B1)); when one of the sialic acid residues was lactonized and the other sialic acid residue was isopropylamidated, a peak was observed at m/z 2347 (FIGS. 3(B2) and 3(B3); and when the two sialic acid residues were both isopropylamidated, a peak was observed at m/z 2406 (FIG. 3(B4)).

These results reveal that the method according to the present invention makes it possible to determine the number of sialic acid residues in a sugar chain and identify the linkage type of sialic acid. When ethylamine hydrochloride was used, even in the case of the sugar chain having only α2,3-linked sialic acid residues, a peak was observed also at m/z 2333 which was derived from an ethylamidated product (FIG. 3(A1)), and even in the case of the sugar chain having only one α2,3-linked sialic acid residue, a peak was observed also at m/z 2338 (FIGS. 3(A2) and 3(A3)), which indicates that some α2,3-linked sialic acid residues were ethylamidated. In contrast, when isopropylamine hydrochloride was used, almost one signal was observed for all the sugar chain samples (FIGS. 3(B1) to 3(B4)) because isopropylamine was high in reaction specificity depending on the linkage type of sialic acid. These results reveal that even when the type of sugar chain is different, the specificity for lactone formation depending on the type of amine used etc., which was examined in Examples 1 and 2 described above, is maintained.

[Example 4] Modification of Sugar Chains Released from Glycoprotein

In Example 4, free sugar chains released from fetuin, which has high α2,3-sialyl sugar chain content, were modified.

(Release of Sugar Chains from Glycoprotein and Purification of Sugar Chains)

A glycoprotein (fetuin) was dissolved in 20 mM ammonium bicarbonate, 10 mM DTT, and 0.02% SDS, and denatured/reduced by treatment at 100° C. for 3 minutes. Then, the solution was cooled to room temperature, and PNGase F was added to release sugar chains by incubation at 37° C. overnight. On the next day, heat treatment was performed at 100° C. for 3 minutes to deactivate PNGase F to stop the enzymatic reaction.

The sugar chains released by the enzymatic reaction were desalted and purified using a carbon column. As the carbon column, Stage Tip Carbon was used which was prepared by packing Empore disk carbon (manufactured by 3M) cut to have a diameter of about 1 mm in a 200-μL pipette tip. 100 μL of ACN was added to Stage Tip Carbon and then passed through by centrifugation. Thereafter, the same operation was repeated using 1 M NaOH, 1 M HCl, water, a 60% ACN, 0.1% TFA solution, and water in this order to wash and equilibrate the column carrier. Then, an enzymatic reaction solution was added to the column, and the solution was loaded by centrifugation. Thereafter, 200 μL of water was added and passed through by centrifugation, which was repeated three times to perform washing. Finally, 20 μL of a 60% ACN, 0.1% TFA solution was added and passed through by centrifugation, which was repeated twice to elute the sugar chains. The thus obtained two eluates were mixed and dried to remove the solvent by SpeedVac.

Comparative Example 4-1: Methylamidation

To the dried sample, 10 μL of a solution obtained by dissolving 4 M methylamine hydrochloride in DMSO was added. Then, 10 μL of a solution obtained by dissolving 250 mM PyAOP in 30% N-methylmorpholine (NMM) was added, and the mixture was stirred at room temperature for 1 hour. To the solution after the reaction, 120 μL of a 93.3% ACN, 0.13% TFA solution was added. Then, using GL-Tip Amide, purification and elution were performed in the same manner as those performed after reaction with isopropylamine, and the eluate was dried by SpeedVac.

The dried sample was redissolved in 10 μL of water, 1 μL of the sample solution was dropped onto a focus plate, 0.5 μL of a solution obtained by dissolving 100 mM 3AQ/CA and 2 mM ammonium sulfate in 50% ACN was added as a matrix, and then the mixture was reacted on a heat block at 75° C. for 1.5 hours to label the reducing ends of the sugar chins with 3AQ. After the completion of the reaction, the plate was cooled to room temperature and subjected to mass spectrometry in negative ion mode by MALDI-QIT-TOF-MS (AXIMA-Resonance, Shimadzu/Kratos). The obtained mass spectrum is shown in FIG. 4(A).

Example 4-1: Methylamidation after Lactonization Using Isopropylamine (Reaction with Isopropylamine)

The sugar chains were modified using DIC and HOBt as a dehydration-condensation agent and isopropylamine hydrochloride as an amine hydrochloride in the same manner as in Example 1, and then the solution after the reaction was diluted by adding 120 μL of a 93.3% ACN, 0.13% TFA solution.

As a carrier for purification, GL-Tip Amide (manufactured by GL Science) was used. First, 100 μL of water was added to GL-Tip Amide and passed through by centrifugation, which was repeated three times to perform washing. Then, 100 μL of a 90% ACN, 0.1% TFA solution was added and passed through by centrifugation, which was repeated three times to perform equilibration. Then, all the diluted reaction solution was added to adsorb the sugar chains to the carrier, followed by centrifugation. Thereafter, 200 μL of a 90% ACN, 0.1% TFA solution was added and passed through by centrifugation, which was repeated three times to perform washing. Finally, 10 μL of water was added and passed through by centrifugation, which was repeated twice to elute the sugar chains. The thus obtained two eluates were mixed and dried by removing the solvent by SpeedVac.

(Methylamidation)

To the dried sample, 10 μL of a solution obtained by dissolving 4 M methylamine hydrochloride in DMSO was added. Then, 10 μL of a solution obtained by dissolving 100 mM PyAOP in 60% N-methylmorpholine (NMM) was added, and the mixture was stirred at room temperature for 1 hour. Further, 5 μL of a solution obtained by dissolving 500 mM PyAOP in 30% NMM/DMSO was added, and the mixture was stirred at room temperature for 1 hour. To the solution after the reaction, 120 μL of a 93.3% ACN, 0.13% TFA solution was added. Then, using GL-Tip Amide, purification and elution were performed in the same manner as those performed after reaction with isopropylamine, and the eluate was dried by SpeedVac.

(Mass Spectrometry)

Figure 4:
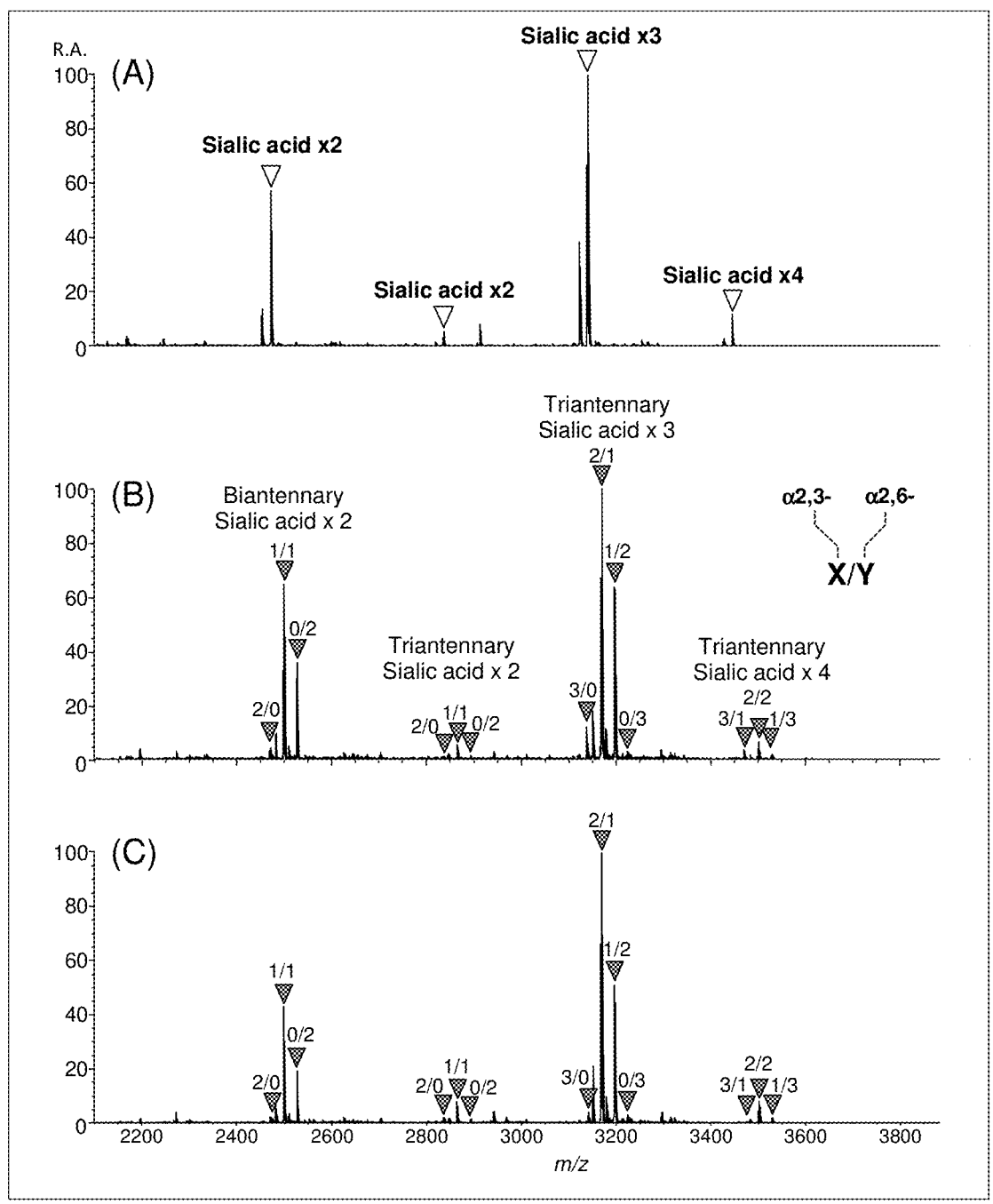

The dried sample was redissolved in 10 μL of water, and 1 μL of the sample solution was dropped on a focus plate and subjected to mass spectrometry in negative ion mode in the same manner as in Comparative Example 4-1. The obtained mass spectrum is shown in FIG. 4 (B).

(Results of Analysis)

In Comparative Example 4-1 in which only methylamidation using PyAOP was performed, the linkage type of sialic acid could not be identified, and only signals corresponding to the number of sialic acid residues were observed. On the other hand, in Example 4-1 in which the reaction with isopropylamine hydrochloride was performed in the presence of DIC and HOBt as a dehydration-condensation agent and then the reaction with methylamine hydrochloride was performed in the presence of PyAOP, peaks were observed at different m/z depending on the linkage type of sialic acid and the number of sialic acid residues. These results indicate that isopropylamidated sugar chains, methylamidated sugar chains, and sugar chains having both of them in the molecule were formed. These results reveal that derivatization makes it possible not only to identify the linkage type of sialic acid but also to quantitatively determine the relative proportion of the sugar chains.

Figure 5:
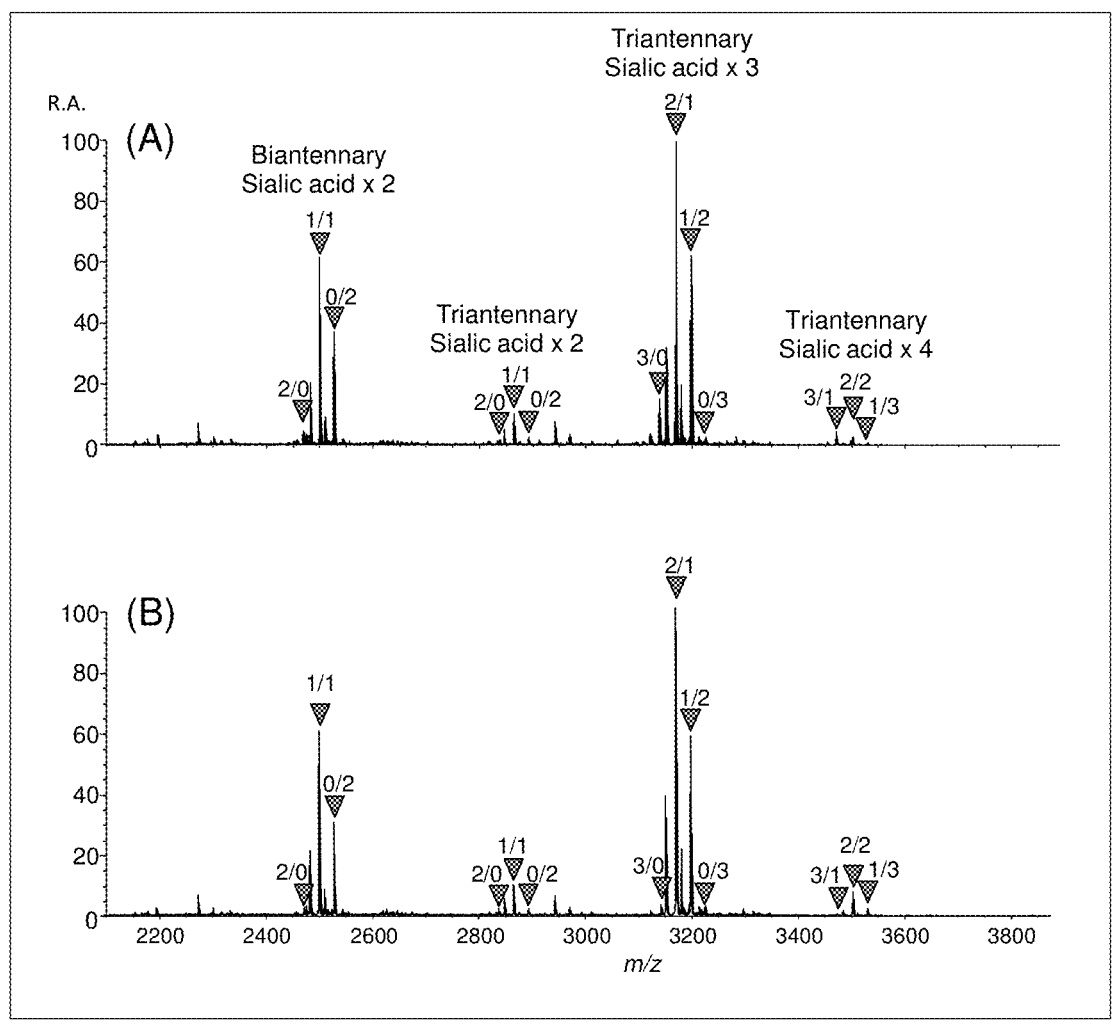

It is to be noted that X and Y in X/Y shown in FIG. 4(B) represents the number of α2,3-linked sialic acid residues and the number of α2,6-linked sialic acid residues, respectively (the same applies to FIG. 4(C) and FIG. 5). For example, peaks derived from triantennary sugar chains having three sialic acid residues are observed at about m/z 3200, and the peak of the sugar chain whose three sialic acid residues are all α2,3-linked sialic acid residues (3/0) has the smallest m/z, and the peak of the sugar chain whose three sialic acid residues are all α2,6-linked sialic acid residues (0/3) has the largest m/z.

The mass difference between the isopropylamidated product and the lactonized product was 59 Da, whereas the difference in m/z between the modified product of an α2,3-sialyl sugar chain and the modified product of an α2,6-sialyl sugar chain was 28 in the example in which the reaction with methylamine as the second reaction was performed after the first reaction with isopropylamine (FIG. 4(B); for example, the difference in m/z between the biantennary sugar chain (2/0) and the biantennary sugar chain (1/1) was 28, and the difference in m/z between the biantennary sugar chain (2/0) and the biantennary sugar chain (0/2) was 56). The difference of 28 Da is equal to the difference between an isopropyl group and a methyl group (=ethylene: $C_2H_4$). This reveals that the α2,3-sialyl sugar chain was lactonized by the reaction with isopropylamine and then methylamidated by lactone ring opening caused by the reaction with methylamine in the presence of PyAOP. It is revealed, on the other hand, that the α2,6-sialyl sugar chain was isopropylamidated by the reaction with isopropylamine, but was not reacted with methylamine in the presence of PyAOP and therefore remained isopropylamidated (see also Example 4-4 that will be described later).

These results reveal that when sugar chains are reacted with an amine in the presence of a dehydration-condensation agent to lactonize α2,3-sialyl sugar chains and amidate α2,6-sialyl sugar chains, and are then further subjected to the second reaction with another amine, lactones derived from the α2,3-sialyl sugar chains are amidated by ring opening so that amidated products having molecular weights different from those of amidated products derived from the α2,6-sialyl sugar chains are formed, which makes it possible to identify the linkage types of the sugar chains by mass spectrometry. Further, in FIG. 4(B), almost no lactone-derived signals were observed, which reveals that the lactones were amidated with high reaction efficiency by this method.

Example 4-2: Methylamidation of Lactone after Ring Opening by Hydrolysis

In the same manner as in Example 4-1 described above, the sugar chains were modified using DIC, HOBt, and isopropylamine hydrochloride and then purified using GL-Tip Amide to obtain 20 μL of an eluate.

(Ring Opening and Methylamidation of Lactone)
First, 5 μL of a 4.0% aqueous methylamine solution was added to 20 μL of the eluate, and the reaction solution was stirred and was allowed to stand at room temperature for 10 minutes to perform lactone ring opening by hydrolysis. Then, the solution after the reaction was dried by removing the solvent by SpeedVac. After the lactone ring opening in an alkaline environment, methylamidation was performed with stirring in the presence of NMM and PyAOP, and purification and sample drying were performed in the same manner as in Example 4-1 described above.

(Mass Spectrometry)
The dried sample was redissolved in 10 μL of water, and subjected to mass spectrometry in negative ion mode in the same manner as in Example 4-1. The obtained mass spectrum is shown in FIG. 4 (C).

(Results of Analysis)
The mass spectrum shown in FIG. 4(C) was similar to that shown in FIG. 4(B), but the number of signals observed in FIG. 4(C) was smaller than that observed in FIG. 4 (B). Even when the concentration of the aqueous methylamine solution used for the lactone ring-opening reaction was changed from 4.0% (methylamine concentration in the reaction solution: 0.8%) to 40% (methylamine concentration in the reaction solution: 8%), a mass spectrum almost similar to that shown in FIG. 4(C) was obtained, and the number of peaks observed in the mass spectrum was smaller than that observed in FIG. 4 (B). This is due to the complete disappearance of lactone-derived signals. These result reveal that the lactone ring opening by hydrolysis (i.e., reaction to return to the state before lactonization by hydrolysis) performed between lactonization (first reaction) using a dehydration-condensation agent and isopropylamine and methylamidation by the second reaction increases the reaction efficiency of methylamidation of α2,3-sialyl sugar chains, which makes it possible to improve analytical accuracy such as quantitativity.

When the concentration of the aqueous methylamine solution was changed to 0.4% (methylamine concentration in the reaction solution: 0.08%), lactone-derived peaks observed in a mass spectrum had lower intensity as compared to those observed in FIG. 4 (B), but did not completely disappear. The lactone can be completely hydrolyzed by increasing the reaction time. However, from the viewpoint of efficiency, it can be said that the concentration of the amine during lactone ring opening is preferably 0.1% or more.

Example 4-3: Modification of Sugar Chain Sample Immobilized on Solid-Phase Carrier The fetuin-derived sugar chains released by enzymatic reaction were immobilized on a solid-phase carrier (Blot-Glyco manufactured by Sumitomo Bakelite Co., Ltd.) having a hydrazide group as a ligand. The binding of the sugar chains was performed in accordance with the standard protocol of BlotGlyco.

(Reaction with Isopropylamine Hydrochloride and Reaction with Methylamine Hydrochloride)
The carrier after the binding of the sugar chains was washed with 200 μL of DMSO three times. Then, 100 μL of an isopropylamidation reaction solution (2 M isopropylamine hydrochloride, 250 mM DIC, 250 mM HOBO was added, mixed gently with a pipette, and reacted at 37° C. for 1.5 hours. The liquid was removed by centrifugation, and then washing with 200 μL of DMSO was repeated three times. Thereafter, 100 μL of a methylamidation reaction solution (2 M methylamine hydrochloride, 50 mM PyAOP, 30% NMM) was added and stirred at room temperature for 1 hour. Then, 5 μL of a PyAOP solution (500 mM PyAOP, 30% NMM) was further added, and the mixture was stirred at room temperature for 30 minutes. Then, washing with 200 μL of DMSO, washing with 200 μL of methanol, and washing with 200 μL of water were each repeated three times. Then, the sugar chain sample after the reaction was liberated from the carrier in accordance with the standard protocol, desalted and purified by Stage Tip Carbon, and dried by SpeedVac.

(Mass Spectrometry)

The dried sample was redissolved in 10 μL of water, and subjected to mass spectrometry in negative ion mode in the same manner as in Example 4-1. The obtained mass spectrum is shown in FIG. 5 (A).

(Results of Analysis)

The spectrum shown in FIG. 5(A) is almost the same as the spectrum shown in FIG. 4(B). This reveals that even when immobilized on a solid-phase carrier, the sugar chains can be modified as with the case where the reaction is performed in a liquid phase state.

Example 4-4: Addition of Lactone Ring-Opening Step in Immobilized State on Solid-Phase Carrier In the same manner as in Example 4-3 described above, the fetuin-derived sugar chains were immobilized on a solid-phase carrier, and a reaction using an isopropylamidation reaction solution and washing with DMSO were performed. Then, lactone ring opening was performed in an alkaline environment by washing with 200 μL of a 1% aqueous methylamine solution three times. Thereafter, in the same manner as in Example 4-3 described above, amidation was performed using a methylamidation reaction solution, and the sample liberated from the solid-phase carrier was purified and subjected to negative ion mode mass spectrometry. The obtained mass spectrum is shown in FIG. 5(B).

(Results of Analysis)

The spectrum shown in FIG. 5(B) was similar to the spectrum shown in FIG. 4(C), and the number of signals observed in FIG. 5(B) was smaller than that observed in FIG. 5(A). This result reveals that even when the sugar chains are immobilized on a solid phase, the reaction efficiency of methylamidation of α2,3-sialyl sugar chains is increased by performing hydrolysis-induced lactone ring opening between lactonization (first reaction) and methylamidation by the second reaction. Further, there is no change in the overall signal intensity between FIG. 5(A) and FIG. 5(B). This reveals that even when washing with an amine is performed for lactone ring opening, the sugar chains can be kept immobilized on the carrier without causing the cleavage of hydrazone of the carrier due to an increase in pH.

Example 4-5

As a glycoprotein, transferrin mainly containing α2,6-sialyl sugar chains was used instead of fetuin, and sugar chains were released from transferrin by enzymatic reaction using PNGase F. In the same manner as in Examples 4-1 to 4-3 described above, the reaction with isopropylamine hydrochloride followed by the reaction with methylamine hydrochloride was performed, and then mass spectrometry was performed in negative ion mode.

In either case where the reactions were performed in a liquid phase in the same manner as in Example 4-1 using the sugar chains released from transferrin or where the reactions were performed in a solid phase state in which the sugar chains were immobilized on a carrier in the same manner as in Example 4-3, only peaks derived from isopropylamidated products of sialyl sugar chains were observed in a mass spectrum. Also in a case where a sample is allowed to stand in an aqueous methylamine solution between the reaction using isopropylamine hydrochloride and the reaction using methylamine hydrochloride as in the same manner as in Example 4-2, only peaks derived from isopropylamidated products were observed. This reveals that almost all α2,6-linked sialic acid residues were isopropylamidated by reaction with isopropylamine hydrochloride using DIC and HOBt as a dehydration-condensation agent, and the obtained isopropylamidated products were not reacted even by adding PyAOP and methylamine later.

[Example 5] Modification of Sialylglycopeptide

In Example 5, modification of a glycopeptide was performed using sialylglycopeptide (SGP) as the glycopeptide.

Example 5-1; Modification of Sialylglycopeptide with Isopropylamine (Modification of Glycopeptide and Purification)

2,3-SGP and 2,6-SGP (both of which are glycopeptide reference standards manufactured by FUSHIMI Pharmaceutical Co., Ltd.; 2865.8 Da) were each dissolved in water, dispensed in aliquots of 100 pmol, and subjected to solvent removal by SpeedVac. Thereafter, 10 μL of a 4 M isopropylamine hydrochloride DMSO solution was added thereto, and then 10 μL of a DMSO solution of 100 mM DIC and 100 mM HOBt was added, and the mixture was stirred at room temperature for 2 minutes and then reacted at 37° C. for 1 hour. The solution after the reaction was diluted by adding 120 μL of a 93.3% ACN, 0.13% TFA solution. Then, purification was performed using cotton HILIC microtip in the same manner as in Example 1 to elute the sugar chain into water.

(Mass Spectrometry)

First, 1 μL of the eluted sample in water was dropped onto a focus plate, and 0.5 μL of a solution obtained by dissolving 10 mg/mL 2',4',6'-trihydroxyacetophenone monohydrate (THAP) in 50% ACN was added as a matrix. Mass spectrometry was performed in negative ion mode by MALDI-QIT-TOF-MS (AXIMA-Resonance, Shimadzu/Kratos). The negative ion mass spectrum of a reaction product of 2,3-SGP is shown in FIG. 6-1(A). The negative ion mass spectrum of a reaction product of 2,6-SGP is shown in FIG. 6-1(B).

Mass spectrometry was performed in positive ion mode by changing the matrix to a solution obtained by dissolving 10 mg/mL 2,5-dihydroxybenzoic acid (DHB) and 0.1 mM methylenediphosphonic acid (MDPNA) in 50% ACN. The positive ion mass spectrum of a reaction product of 2,3-SGP is shown in FIG. 6-2(A). The positive ion mass spectrum of a reaction product of 2,6-SGP is shown in FIG. 6-2(B).

(Results of Analysis)

In the negative ion mass spectrum of a reaction product of 2,3-SGP (FIG. 6-1(A)), a peak was observed at m/z 2827, and in the negative ion mass spectrum of a reaction product of 2,6-SGP (FIG. 6-1(B)), a peak was observed at m/z 2945. The difference in m/z between them is 118, which corresponds to two isopropylamine moieties. This reveals that two sialic acid residues of 2,3-SGP were both modified by lactonization, and two sialic acid residues of 2,6-SGP were both modified by isopropylamidation. These results reveal that the method according to the present invention is useful to identify and quantitatively determine the linkage type of sialic acid of not only a free sugar chain but also a sugar chain of a glycopeptide.

In the positive ion mass spectrum of a reaction product of 2,3-SGP (FIG. 6-2(A)), a peak was observed at m/z 2829, and in the positive ion mass spectrum of a reaction product of 2,6-SGP (FIG. 6-2(B)), a peak was observed at m/z 2947. The difference in m/z between them is 118, which was identical to the case of the negative ion mass spectra. It is to be noted that although a peak of m/z 2847 ([MH]$^+$+18) was observed, which is considered due to the ring opening of one of two lactone rings by hydrolysis during ionization, in the positive ion mass spectrum of a reaction product of 2,3-SGP, the intensity of the peak was sufficiently lower than that of the peak of [MH]$^+$. Peaks were observed also at m/z 2929 ([MH]$^+$−18) and m/z 2988 ([MH]$^+$+41) in the positive ion mass spectrum of a reaction product of 2,6-SGP. The former was derived from a dehydrated product of the isopropylamidated product and the latter was derived from the peptide whose carboxy group at the C-terminus was isopropylamidated, both of which could be identified.

These results reveal that the modification method according to the present invention can be applied to both positive ion mode mass spectrometry and negative ion mode mass spectrometry of glycopeptides, and the linkage type of sialic acid of a sugar chain can be identified in either positive ion mode or negative ion mode.

It is to be noted that the difference in m/z value between the peak in the mass spectrum obtained in this example and the peak of the sialylglycopeptide before modification in either positive ion mode or negative ion mode was −36 when two sialic acid residues were lactonized by dehydration (FIGS. 6-1(A) and 6-2(A)), and was +82 when two sialic acid residues were isopropylamidated (FIGS. 6-1(B) and 6-2(B)). These results reveal that even when the sialylglycopeptide was reacted with an amine hydrochloride in the presence of a dehydration-condensation agent, the carboxy group at the C-terminus of the peptide was hardly modified.

Example 5-2: Confirmation of Modified Site by in-Source Decay Mass Spectrometry

For the purpose of confirming that in Example 5-1 described above, a site modified with isopropylamine was a sialic acid site of the sugar chain and the peptide moiety was not modified, glycopeptide were subjected to fragment ion measurement. Specifically, in-source decay was promoted by increasing laser intensity during positive ion mode mass spectrometry to generate fragment ions to determine fragments in the low m/z region. The in-source decay mass spectrum of reaction product of 2,3-SGP is shown in FIG. 7(A), and the in-source decay mass spectrum of reaction product of 2,6-SGP is shown in FIG. 7(B).

Figure 7:
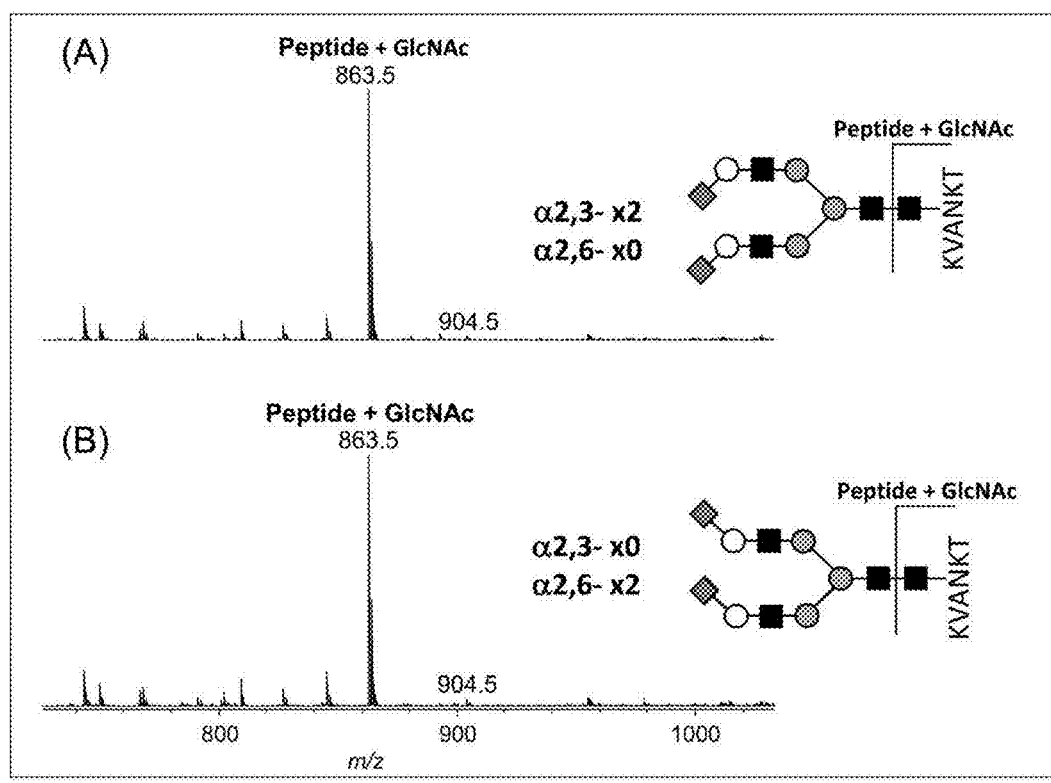
FIG. 7(A) is an in-source decay mass spectrum (low m/z region) of a reaction product between 2,3-SGP and isopropylamine.
FIG. 7(B) is an in-source decay mass spectrum (low m/z region) of a reaction product between 2,6-SGP and isopropylamine.

In both the cases of a reaction product of 2,3-SGP and a reaction product of 2,6-SGP, a clear signal of m/z 863.5 was observed in the low m/z region, and there was no difference in the m/z of a fragment ion between them. The peak at m/z 863.5 is derived from an ion in which one GlcNAc residue is added to the peptide. This ion is a fragment that is often observed as a fragment ion of a glycopeptide. As shown in FIG. 6-2, the difference in m/z between the reaction product of 2,3-SGP and the reaction product of 2,6-SGP was 118, and as shown in FIG. 7, there was no difference in m/z between the peptide moieties of both the reaction products, which reveals that the peptide moieties were hardly modified.

In FIGS. 7(A) and 7(B), a signal of m/z 904.5 derived from a fragment in which the carboxy group at the C-terminus of the peptide was amidated by isopropylamine was detected, but the intensity of the signal was less than 3% of the intensity of the signal of m/z 863.5 derived from the fragment in which the peptide moiety was not modified. These results reveal that when the glycopeptide was reacted with an amine hydrochloride in the presence of a dehydration-condensation agent, the carboxy group at the C-terminus of the peptide was hardly modified, and the sialic acid moiety of the sugar chain was selectively modified.

Figure 8:
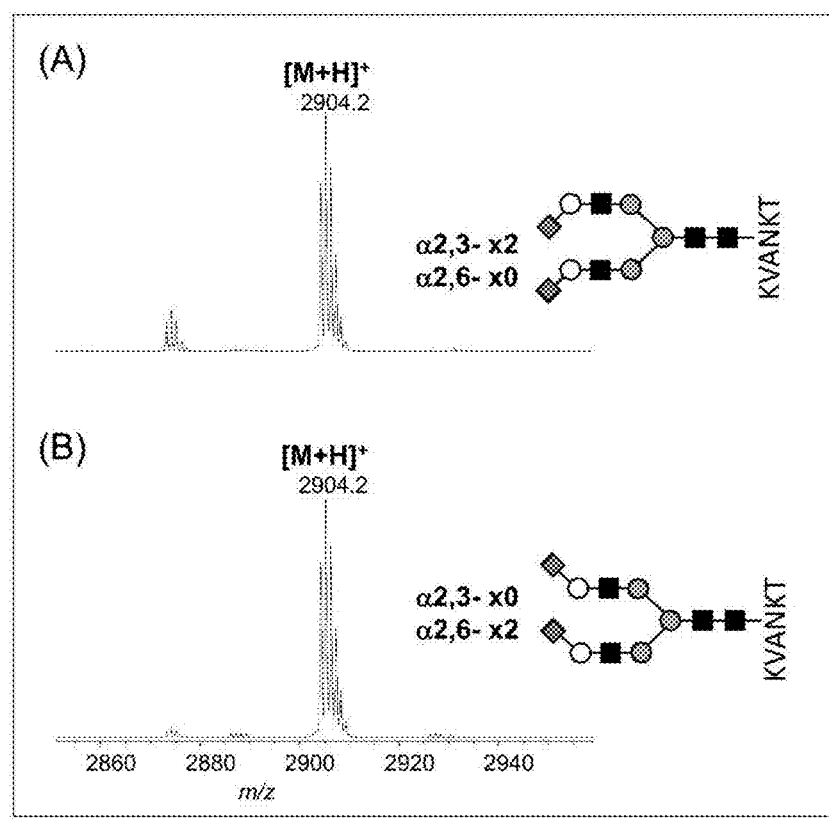
FIG. 8 (A) is a positive ion mass spectrum of a reaction product between 2,3-SGP and methylamine, and FIG. 6-2 (B) is a positive ion mass spectrum of a reaction product between 2,6-SGP and methylamine.

Comparative Example 5-1: Modification of Sialylglycopeptide with Methylamine 2,3-SGP and 2,6-SGP were each dissolved in water, dispensed in aliquots of 100 pmol, and subjected to solvent removal by SpeedVac. Then, 10 µL of a solution obtained by dissolving 4 M methylamine hydrochloride in DMSO was added thereto. Thereafter, 10 µL of a solution obtained by dissolving 250 mM PyAOP in 30% NMM was added, and the mixture was stirred at room temperature for 1 hour. The reaction product was purified in the same manner as in Example 5-1 described above, and mass spectrometry was performed in positive ion mode. The mass spectrum of the reaction product of 2,3-SGP is shown in FIG. 8(A), and the mass spectrum of the reaction product of 2,6-SGP is shown in FIG. 8(B).

In both the mass spectra of the reaction products of 2,3-SGP and 2,6-SGP with methylamine, a peak was detected at m/z 2904, and there was no difference in m/z depending on the linkage type of sialic acid. The m/z of this peak is larger by 39 than that of a peak derived from the sialylglycopeptide before modification, and this difference corresponds to methylamidation of three carboxy groups contained in the sialylglycopeptide.

In-source decay mass spectrometry of the reaction products of 2,3-SGP and 2,6-SGP with methylamine was performed in the same manner as in Example 5-2 (data is not shown). As a result, a clear signal was observed at m/z 876.5 larger by 13 than that of an ion in which one GlcNAc residue was added to the peptide, which reveals that a fragment in which one site of the peptide moiety (the carboxy group at the C-terminus) was methylamidated was generated. On the other hand, a signal at m/z 863.5 was hardly observed.

From these results, it can be said that all the three carboxy groups in two sialic acid sites and at the C-terminus of the peptide moiety were methylamidated by the reaction of the sialylglycopeptide with methylamine irrespective of the linkage type of sialic acid, and therefore it is difficult to identify the linkage type of sialic acid.

Comparative Example 5-2: Modification of Sialylglycopeptide with Ethanol

Figure 9:
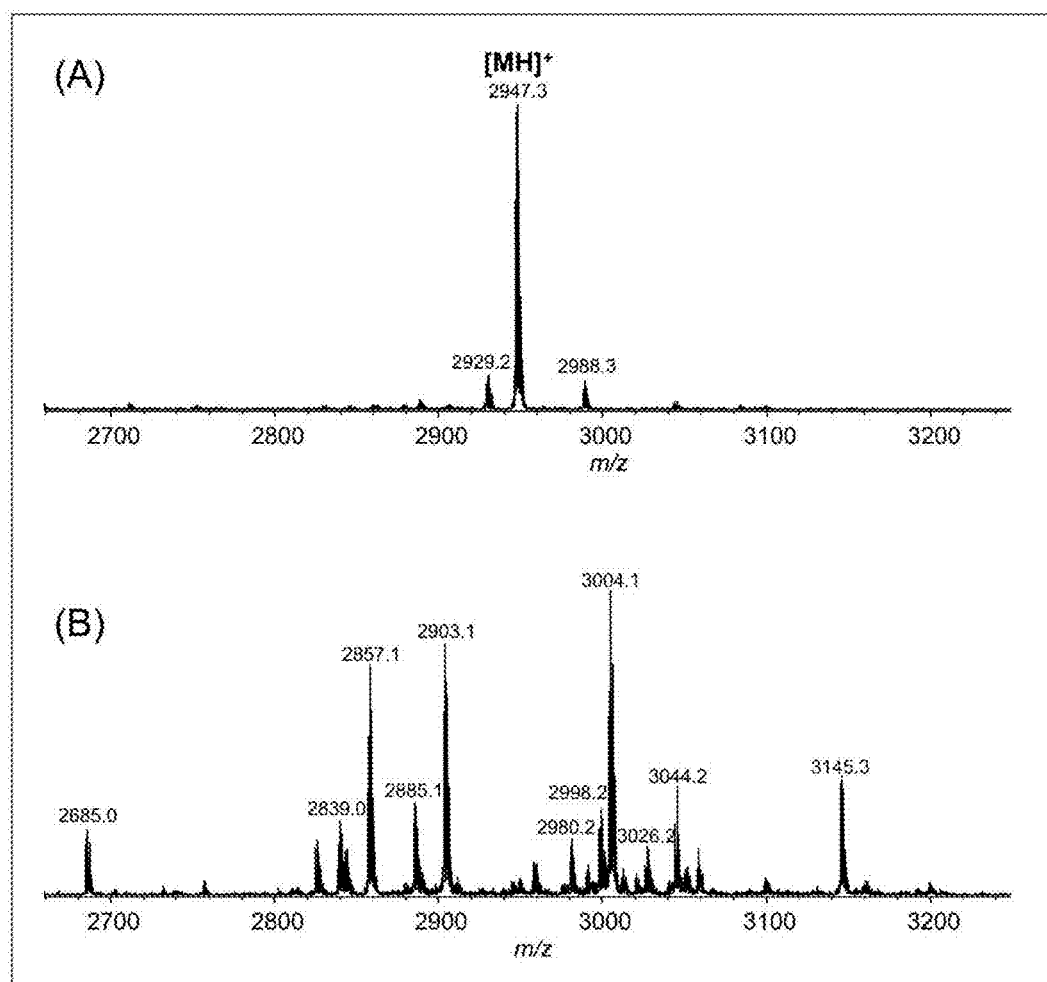
FIG. 9(A) is a positive ion mass spectrum of a reaction product between 2,6-SGP and isopropylamine.
FIG. 9(B) is a positive ion mass spectrum of a reaction product between 2,6-SGP and ethanol.

Modification of 2,6-SGP was performed in ethanol containing 1-ethyl-3-(3-(dimethylamino)propyl)carbodiimide (EDC) and HOBt as a dehydration-condensation agent by a method described in Reiding, K. et al, *Anal. Chem.*, Vol. 86, pp. 5784-5793 (2014) (Non-Patent Document 2), and mass spectrometry was performed in positive ion mode in the same manner as in Example 5-1. The mass spectrum of 2,6-SGP modified with ethanol is shown in FIG. 9(B). For comparison, the mass spectrum of 2,6-SGP modified with isopropylamine (Example 5-1) is shown in FIG. 9(A).

In the mass spectrum of the sample modified with ethanol (FIG. 9(B)), the signal of a possible ethyl-esterified product was not observed at m/z 2394, and many side reaction signals were observed. These results reveal that esterification of sialic acid can be used for analysis of free sugar chains, but is difficult to be applied to analysis of glycopeptides.

[Example 6] Reaction of Sialic Acid-Free Glycopeptide with Amine

In Example 6, in order to confirm that when a glycopeptide is reacted with isopropylamine in the presence of a dehydration-condensation agent, the sialic acid site of a sugar chain is selectively modified, and a peptide moiety is hardly reacted (the results of Example 5 described above), a verification test was performed using sialic acid-free glycopeptides. As the glycopeptides, a digest of RNase B and a digest of IgG were used.

(Preparation of Glycopeptide Sample)

RNase B and IgG (both of which were purchased from SIGMA) were each treated at room temperature for 45 minutes in the presence of 6 M urea, 20 mM ammonium bicarbonate, and 5 mM tris(2-carboxyethyl)phosphine hydrochloride (TCEP) to perform denaturation and reduction. Then, reaction was performed in the presence of 10 mM iodoacetamide (IAA) at room temperature under light-tight conditions for 45 minutes to perform alkylation. Then, DTT was added to a concentration of 10 mM, and reaction was performed at room temperature under light-tight conditions for 45 minutes to deactivate excess IAA. Thereafter, trypsin was added, and incubation was performed at 37° C. overnight for protease digestion. After the digestion, the digest was desalted using a carbon column and dried by SpeedVac.

(Reaction with Isopropylamine and Mass Spectrometry)
(Purification of Reaction Product and Mass Spectrometry)

Figure 10:
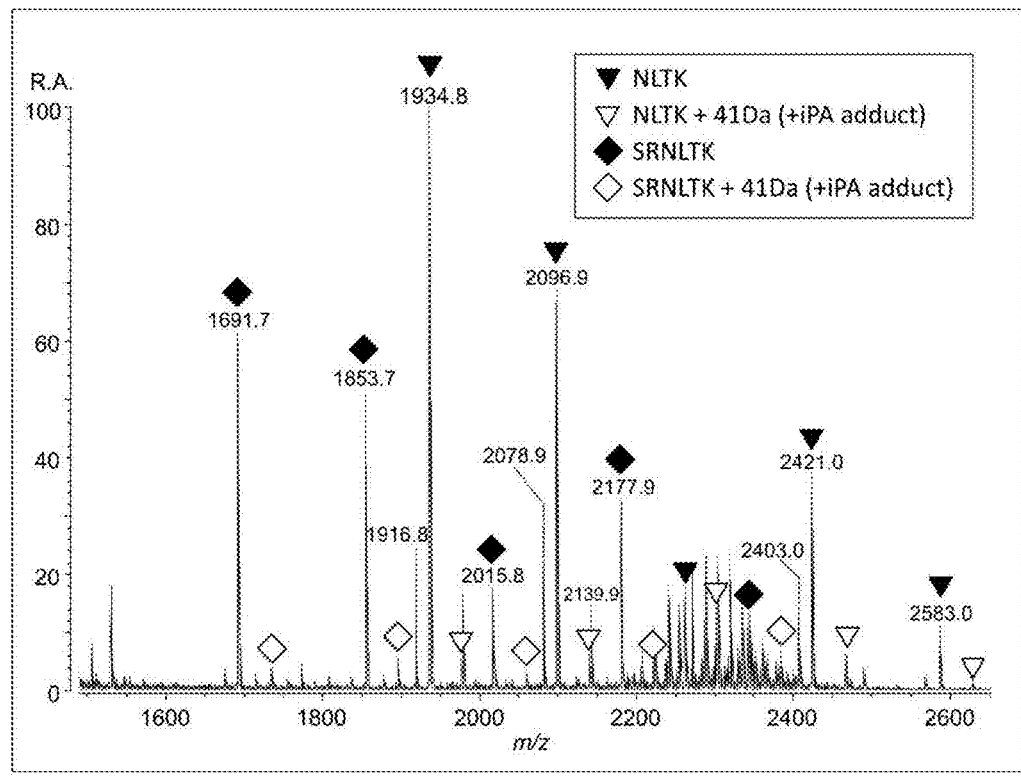
FIG. 10 is a positive ion mass spectrum of a reaction product between a digest of RNase B and isopropylamine.
Figure 11:
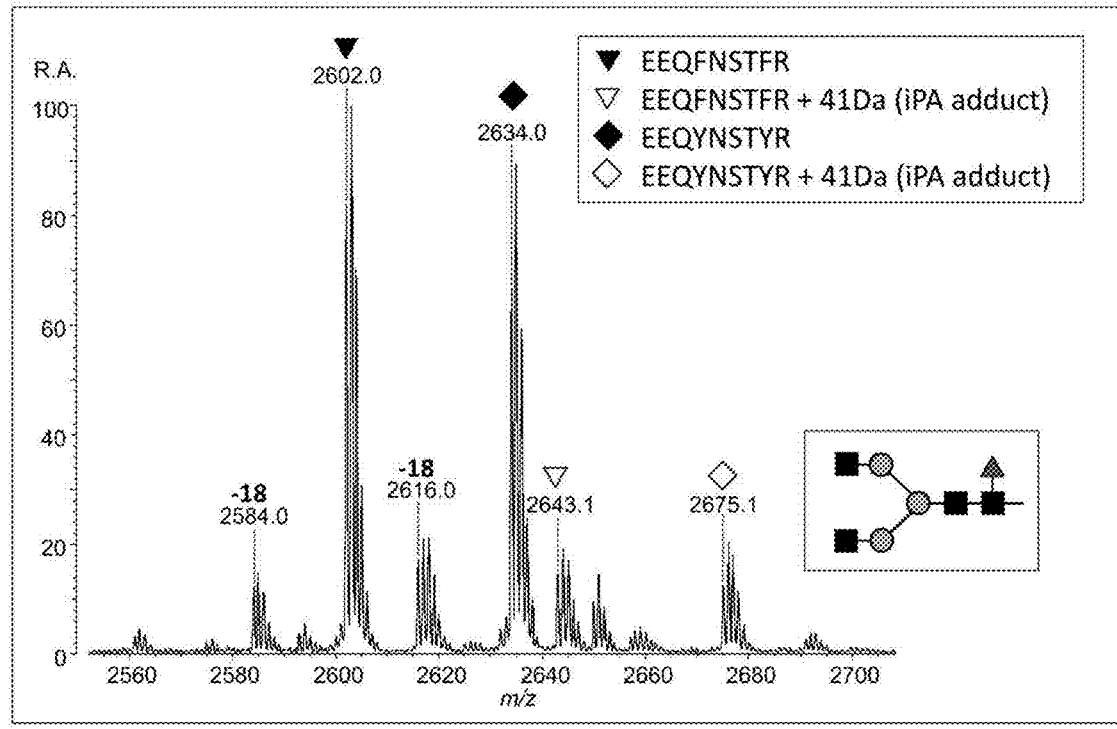
FIG. 11 is a positive ion mass spectrum of a reaction product between a digest of IgG and isopropylamine.

The obtained tryptic digest (glycopeptide) and isopropylamine were reacted in the presence of a dehydration-condensation agent under the same conditions as in Example 5-1, and the reaction product was purified and subjected to mass spectrometry in positive ion mode. The mass spectrum of reaction product of the digest of RNase B is shown in FIG. 10, and the mass spectrum (enlarged view) of reaction product of IgG is shown in FIG. 11.

(Results of Analysis of Reaction Products of RNase B Fragment)

RNase B is a sialic acid-free glycoprotein to which a high mannose-type sugar chain is added. In tryptic digestion of RNase B, missed cleavage occurred in which the C-terminus of arginine of the sequence SRNLTK was not digested. Therefore, as shown in FIG. 10, two types of peptide fragments (NLTK and SRNLTK) were detected. Each of these peptide fragments had five types of high-mannose-type glycoforms (number of mannose residues: 5 to 9), and these glycoforms were observed at intervals of 162 Da.

In this example, the reaction was performed under the same conditions as in Example 5-1. Specifically, under conditions that two sialic acid residues of 2,3 SGP were all lactonized and two sialic acid residues of 2,6-SGP were all isopropylamidated. However, signals were observed at the same m/z as those of the RNase B fragments before reaction. This is because the RNase B fragments do not contain sialic acid. Further, in FIG. 10, signals whose m/z values were larger by 41 than those of the signals of the RNase B fragments before reaction ([MH]$^+$+41: peptides whose C-termini were isopropylamidated (iPA)) were also observed, but the intensities of these signals were about 10% of those of signals of the peptides whose C-termini were not reacted ([MH]$^+$).

(Results of Analysis of Reaction Products of IgG Fragments)

The mass spectrum shown in FIG. 11 contains signals derived from two types of sialic acid-free glycopeptides (derived from subclasses of IgG and having peptide moieties slightly different in amino acid sequence), and strong signals were observed at m/z 2602 and 2634 that were the same as those of signals of the IgG fragments before reaction. Further, in FIG. 11, signals whose m/z values were larger by 41 than those of signals of the IgG fragments before reaction were also observed, but the intensities of these signals were about 20% or less of those of signals of the peptides whose C-termini were not reacted.

As shown in Example 5, when the sugar chain of the glycopeptide contained sialic acid, sialic acid was preferentially modified, and therefore a signal having the same m/z as that of signal of the glycopeptide before reaction was hardly observed. On the other hand, as shown in Example 6, when the sugar chain of the glycopeptide did not contain sialic acid, a high-intensity signal having the same m/z as that of signal of the glycopeptide before reaction was observed regardless of the presence or absence of an acidic amino acid in the peptide moiety. These results reveal that the application of the method according to the present invention to glycopeptides makes it possible to analytically determine the presence or absence of sialic acid, and makes it possible, when a sample contains sialic acid, to identify the linkage type of sialic acid.

The invention claimed is:

1. A sample preparation method for analyzing a sugar chain contained in an analyte, wherein
    the method comprising a first reaction,
        in the first reaction, an analyte containing a sugar chain, an amine containing two or more carbon atoms or a salt thereof, and a dehydration-condensation agent are reacted such that a modified product is formed from a sialic acid in the sugar chain of the analyte,
        when the sugar chain has an α2,3-linked sialic acid, a lactone is formed as the modified product by the first reaction, and
        when the sugar chain has an α2,6-linked sialic acid, an amide is formed as the modified product by the first reaction,
    wherein the dehydration-condensation agent includes a carbodiimide and at least one nucleophilic additive selected from the group consisting of 1-hydroxybenzotriazole, 1-hydroxy-7-aza-benzotriazole, 4-(dimethylamino)pyridine, ethyl 2-cyano-2-(hydroxyimino)acetate, N-hydroxy-succinimide, 6-chloro-1-hydroxybenzotriazole, and N-hydroxy-3,4-dihydro-4-oxo-1,2,3-benzotriazine.

2. The sample preparation method according to claim 1, wherein the amine is an alkylamine having a branched alkyl group or a salt thereof.

3. The sample preparation method according to claim 1, wherein the amine is a primary alkylamine or a salt thereof.

4. The sample preparation method according to claim 1, wherein the amine is isopropylamine or a salt thereof.

5. The sample preparation method according to claim 1, wherein the first reaction is performed in a state where the analyte is immobilized on a solid-phase carrier.

6. The sample preparation method according to claim 1, further comprising a step of subjecting the analyte after the first reaction to a second reaction, wherein
the second reaction is a reaction in which when a lactone formed from the analyte by the first reaction is present, another modified product is formed from the lactone.

7. The sample preparation method according to claim 6, wherein the second reaction is a reaction in which an amide is formed from the lactone, and
an amine used in the second reaction is selected such that an amide that can be formed by the first reaction from α2,6-linked sialic acid and the amide that can be formed by the second reaction from the lactone derived from α2,3-linked sialic acid have different masses.

8. The sample preparation method according to claim 7, wherein
in addition to the amine, a phosphonium-based dehydration-condensation agent or an uronium-based dehydration-condensation agent is used in the second reaction.

9. The sample preparation method according to claim 6, wherein the second reaction is performed in a state where the analyte after the first reaction is immobilized on a solid-phase carrier.

10. The sample preparation method according to claim 1, wherein the analyte is a glycopeptide or a glycoprotein.

11. An analysis method comprising: preparing a sample by the sample preparation method according to claim 1; and analyzing the sample prepared by the sample preparation method.

12. The analysis method according to claim 11, wherein the sample is analyzed by mass spectrometry.

13. An analysis method comprising: preparing a sample by the sample preparation method according to claim 6; and analyzing the sample prepared by the sample preparation method.

14. The analysis method according to claim 13, wherein the sample is analyzed by mass spectrometry.

15. The sample preparation method according to claim 6, wherein the second reaction is a reaction in which an amide is formed from the lactone, and
an amine used in the first reaction or the second reaction is selected from an isotope-labeled amine.

* * * * *